(12) United States Patent
Lee et al.

(10) Patent No.: US 8,395,143 B2
(45) Date of Patent: Mar. 12, 2013

(54) COMPOUND AND ORGANIC LIGHT EMITTING DEVICE USING THE SAME

(75) Inventors: Jae-Chol Lee, Daejeon (KR); Kong-Kyeom Kim, Daejeon (KR); Sung-Kil Hong, Daejeon (KR); Tae-Yoon Park, Daejeon (KR)

(73) Assignee: LG Chem, Ltd., Seoul (KR)

( * ) Notice: Subject to any disclaimer, the term of this patent is extended or adjusted under 35 U.S.C. 154(b) by 215 days.

(21) Appl. No.: 12/742,069

(22) PCT Filed: Nov. 7, 2008

(86) PCT No.: PCT/KR2008/006564
§ 371 (c)(1),
(2), (4) Date: May 7, 2010

(87) PCT Pub. No.: WO2009/061145
PCT Pub. Date: May 14, 2009

(65) Prior Publication Data
US 2010/0244008 A1 Sep. 30, 2010

(30) Foreign Application Priority Data

Nov. 8, 2007 (KR) .................. 10-2007-0113852
Jul. 25, 2008 (KR) .................. 10-2008-0073238

(51) Int. Cl.
*H01L 51/54* (2006.01)

(52) U.S. Cl. ........... 257/40; 257/E51.026; 257/E51.024; 257/E51.049
(58) Field of Classification Search ............ 257/40, 257/E51.026
See application file for complete search history.

(56) References Cited

U.S. PATENT DOCUMENTS

| 7,737,627 B2 | 6/2010 | Hwang et al. |
| 2005/0221124 A1 | 10/2005 | Hwang et al. |
| 2007/0049760 A1 | 3/2007 | Kawakami et al. |
| 2007/0231503 A1 | 10/2007 | Hwang et al. |
| 2008/0124572 A1 | 5/2008 | Mizuki et al. |

FOREIGN PATENT DOCUMENTS

| EP | 1205527 | 5/2002 |
| EP | 2085382 | 8/2009 |
| JP | 9-310066 A | 12/1997 |
| JP | 09-310066 A | 12/1997 |
| JP | 2003-133075 A | 5/2003 |
| KR | 0573137 | 4/2006 |
| WO | WO 01/72927 A1 | 10/2001 |
| WO | WO 2005-090512 A1 | 9/2005 |
| WO | WO 2006-043647 A1 | 4/2006 |

*Primary Examiner* — Mamadou Diallo
(74) *Attorney, Agent, or Firm* — McKenna Long & Aldridge LLP

(57) ABSTRACT

The present invention provides a novel compound that is capable of largely improving lifespan, efficiency, electrochemical stability and thermal stability of the organic light emitting device, and an organic light emitting device in which the compound is included in an organic compound layer.

12 Claims, 1 Drawing Sheet

COMPOUND AND ORGANIC LIGHT EMITTING DEVICE USING THE SAME

This application is a 35 U.S.C. §371 National Stage entry of International Application No. PCT/KR2008/006564, filed on Nov. 7, 2008, and claims priority to Korean Application No. 10-2007-0113852, filed on Nov. 8, 2007 and Korean Application No. 10-2008-0073238, filed on Jul. 25, 2008, which are all hereby incorporated by reference in their entireties.

TECHNICAL FIELD

The present invention relates to an organic light emitting device in which a novel compound that is capable of largely improving a life span, efficiency, electrochemical stability and thermal stability of the organic light emitting device is included in an organic compound layer. This application claims priority from Korean Patent Application Nos. 10-2007-0113852 and 10-2008-0073238 filed on Nov. 18, 2007 and Jul. 25, 2008, in the KIPO, the disclosure of which is incorporated herein by reference in its entirety.

BACKGROUND ART

An organic light emission phenomenon is an example of a conversion of current into visible rays through an internal process of a specific organic molecule. The organic light emission phenomenon is based on the following mechanism. When organic material layers are interposed between an anode and a cathode, if voltage is applied between the two electrodes, electrons and holes are injected from the cathode and the anode into the organic material layer. The electrons and the holes which are injected into the organic material layer are recombined to form an exciton, and the exciton is reduced to a bottom state to emit light. An organic light emitting device which is based on the above mechanism typiccollectivelyy comprises a cathode, an anode, and organic material layer(s), for example, organic material layers including a hole injection layer, a hole transport layer, a light emitting layer, and an electron transport layer, interposed therebetween.

The materials used in the organic light emitting device are mostly pure organic materials or complexes of organic material and metal. The material used in the organic light emitting device may be classified as a hole injection material, a hole transport material, a light emitting material, an electron transport material, or an electron injection material, according to its use. In connection with this, an organic material having a p-type property, which is easily oxidized and is electrochemiccollectivelyy stable when it is oxidized, is mostly used as the hole injection material or the hole transport material. Meanwhile, an organic material having an n-type property, which is easily reduced and is electrochemiccollectivelyy stable when it is reduced, is used as the electron injection material or the electron transport material. As the light emitting layer material, an organic material having both p-type and n-type properties is preferable, which is stable when it is oxidized and when it is reduced. Also a material having high light emission efficiency for conversion of the exciton into light when the exciton is formed is preferable.

In addition, it is preferable that the material used in the organic light emitting device further have the following properties.

First, it is preferable that the material used in the organic light emitting device have excellent thermal stability. The reason is that joule heat is generated by movement of electric charges in the organic light emitting device. NPB, which has recently been used as the hole transport layer material, has a glass transition temperature of 100° C. or lower, thus it is difficult to apply to an organic light emitting device requiring a high current.

Second, in order to produce an organic light emitting device that is capable of being actuated at low voltage and has high efficiency, holes and electrons which are injected into the organic light emitting device must be smoothly transported to a light emitting layer, and must not be released out of the light emitting layer. To achieve this, a material used in the organic light emitting device must have a proper band gap and a proper HOMO or LUMO energy levels. A LUMO energy level of PEDOT:PSS, which is currently used as a hole transport material of an organic light emitting device produced using a solution coating method, is lower than that of an organic material used as a light emitting layer material, thus it is difficult to produce an organic light emitting device having high efficiency and a long lifespan.

Moreover, the material used in the organic light emitting device must have excellent chemical stability, electric charge mobility, and interfacial characteristic with an electrode or an adjacent layer. That is to say, the material used in the organic light emitting device must be little deformed by moisture or oxygen. Furthermore, proper hole or electron mobility must be assured so as to balance densities of the holes and of the electrons in the light emitting layer of the organic light emitting device to maximize the formation of excitons. Additionally, it has to be able to have a good interface with an electrode including metal or metal oxides so as to assure stability of the device.

Accordingly, there is a need to develop an organic material having the above-mentioned requirements in the art.

DISCLOSURE

Technical Problem

Therefore, the present inventors aim to provide an organic light emitting device that includes a heterocompound derivative which is capable of satisfying conditions required of a material which may be used for an organic light emitting device, for example, a proper energy level, electrochemical stability, and thermal stability, and which has a chemical structure capable of playing various roles required for the organic light emitting device, depending on a substituent group.

Technical Solution

The present invention provides a compound of the following Formula 1.

In addition, the present invention provides an organic light emitting device which comprises a first electrode, organic material layer(s) having one or more layers and comprising a light emitting layer, and a second electrode, wherein the first electrode, the organic material layer(s), and the second electrode form a layered structure and at least one layer of the organic material layer(s) includes a compound of the following Formula 1 or a compound of Formula 1 into which a thermosetting or photo-crosslinkable functional group is introduced:

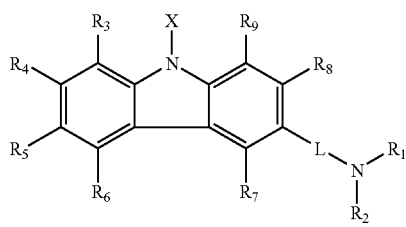

[Formula 1]

wherein X is selected from the group consisting of hydrogen; an alkyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an alkoxy group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an alkenyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an aryl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an hetero ring group including O, N or S as a heteroatom, which is substituted or unsubstituted with one or more substituent groups selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a carbazolyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a fluorenyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; —N(R')(R''); a nitrile group; a nitro group; a halogen group; —CO—N(R')(R''); and —COO—R', R' and R'' are each independently selected from the group consisting of hydrogen, a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group, L is an arylene group having 6 to 40 carbon atoms, which is substituted or unsubstituted with one or more substituent groups selected from the group consisting of nitro, nitrile, halogen, an alkyl group, an alkoxy group and an amino group; a divalent hetero ring group, which is substituted or unsubstituted with one or more substituent groups selected from the group consisting of nitro, nitrile, halogen, an alkyl group, an alkoxy group and an amino group; or a fluorenylene group, which is substituted or unsubstituted with one or more substituent groups selected from the group consisting of nitro, nitrile, halogen, an alkyl group, an alkoxy group and an amino group, $R_1$ and $R_2$ are each independently selected from the group consisting of hydrogen; deuterium; an alkyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an alkoxy group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an alkenyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an aryl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an hetero ring group including O, N or S as a heteroatom, which is substituted or unsubstituted with one or more substituent groups selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a carbazolyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a fluorenyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an aryloxy group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an arylthio group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an alkoxycarbonyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a hydroxyl group; a carboxyl group; a nitrile group; a nitro group; a halogen group; —N(R')(R"); a nitrile group; a nitro group; a halogen group; —CO—N(R')(R"); and —COO—R', and said $R_1$ and $R_2$ may form an aliphatic or hetero condensation ring in conjunction with adjacent groups, and at least one of $R_3$ to $R_9$ is selected from the group consisting of deuterium; an alkenyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluore- nyl group, a nitrile group and an acetylene group; an hetero ring group including O, N or S as a heteroatom, which is substituted or unsubstituted with one or more substituent groups selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a carbazolyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a fluorenyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted aryl alkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a nitrile group; —CO—N(R')(R"); and —COO—R', and said $R_3$ to $R_9$ may form an aliphatic or hetero condensation ring in conjunction with adjacent groups, and the remains of $R_3$ to $R_9$ are selected from hydrogen or deuterium.

[Advantageous Effects]

A compound according to the present invention is configured so that stability in respects to a hole and an electron is increased while properties of carbazole are not largely changed by introducing deuterium to carbazole. These compounds may be used as an organic material layer material, particularly, a hole injection material and/or a hole transport material in an organic light emitting device, and in the case of when it is used in the organic light emitting device, a driving voltage of the device may be reduced, light efficiency may be improved, and a life span property of the device may be improved.

BEST MODE

Figure 1:
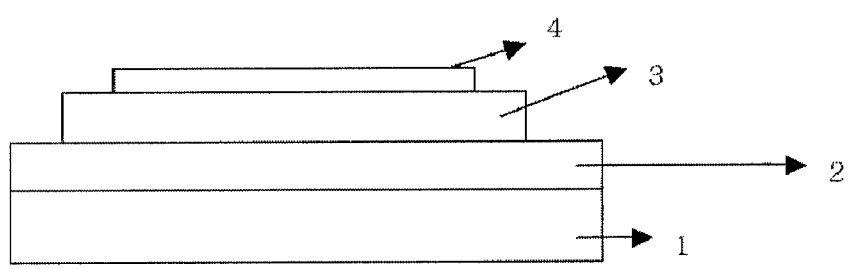
FIG. 1 illustrates an organic light emitting device comprising a substrate 1, an anode 2, a light emitting layer 3, and a cathode 4.
Figure 2:
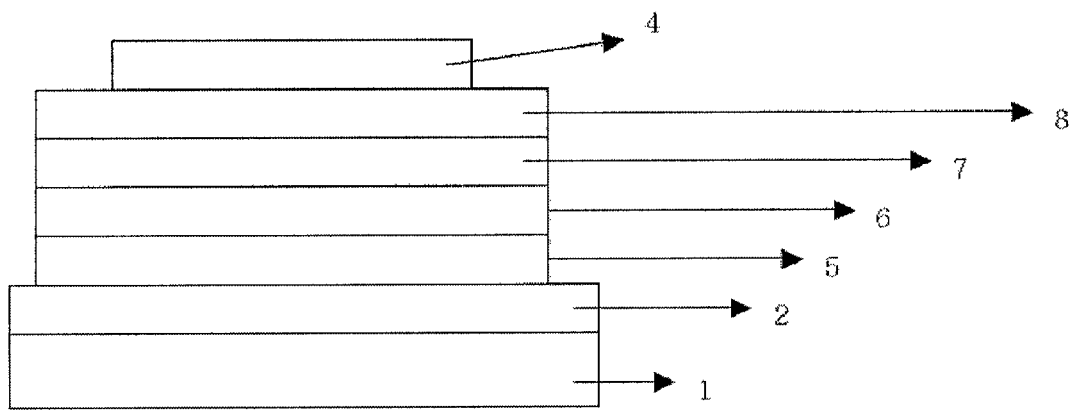
FIG. 2 illustrates an organic light emitting device comprising a substrate 1, an anode 2, a hole injection layer 5, a hole transport layer 6, a light emitting layer 7, an electron transport layer 8, and a cathode 4.

A substituent group of Formula 1 will be described in detail below.

It is preferable that X of Formula 1 is selected from the group consisting of hydrogen; an alkyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an alkoxy group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an alkenyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an aryl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an hetero ring group including O, N or S as a heteroatom, which is substituted or unsubstituted with one or more substituent groups selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a carbazolyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a fluorenyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; —N(R')(R"); a nitrile group; a nitro group; a halogen group; —CO—N(R')(R"); and —COO—R', and it is preferable that R' and R" are each independently selected from the group consisting of hydrogen, a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group.

In addition, in the case of when X of Formula 1 is an aryl group, it maybe selected from a monocyclic aromatic ring, such as a phenyl group, a biphenyl group, a terphenyl group, and a stilbene, and a multicyclic aromatic ring, such as a naphthyl group, an anthracenyl group, a phenanthrene group, a pyrenyl group, and a perylenyl group, and in the case of when X is a hetero ring group, it may be selected from the group consisting of a thiophenyl group, a furan group, a pyrrolyl group, an imidazolyl group, a thiazolyl group, an oxazolyl group, an oxadiazolyl group, a triazolyl group, a pyridyl group, a pyradazine group, a quinolinyl group, an isoquinoline group, and an acridyl group, and may be selected from a carbazolyl group and a fluorenyl group, but not limited thereto.

It is preferable that L of Formula 1 is an arylene group having 6 to 40 carbon atoms, which is substituted or unsubstituted with one or more substituent groups selected from the group consisting of nitro, nitrile, halogen, an alkyl group, an alkoxy group and an amino group; a divalent hetero ring group, which is substituted or unsubstituted with one or more substituent groups selected from the group consisting of nitro, nitrile, halogen, an alkyl group, an alkoxy group and an amino group; or a fluorenylene group, which is substituted or unsubstituted with one or more substituent groups selected from the group consisting of nitro, nitrile, halogen, an alkyl group, an alkoxy group and an amino group.

In addition, it is more preferable that L is a phenylene group, which is substituted or unsubstituted with one or more substituent groups selected from the group consisting of nitro, nitrile, halogen, an alkyl group, an alkoxy group and an amino group; a divalent hetero ring group including O, N or S, and having 5 or 6 carbon atoms, which is substituted or unsubstituted with one or more substituent groups selected from the group consisting of nitro, nitrile, halogen, an alkyl group, an alkoxy group and an amino group; or a fluorenylene group, which is substituted or unsubstituted with one or more substituent groups selected from the group consisting of nitro, nitrile, halogen, an alkyl group, an alkoxy group and an amino group, and it is most preferable that it is a phenylene group or a fluorenylene group.

$R_1$ and $R_2$ of Formula 1 are each independently selected from the group consisting of hydrogen; deuterium; an alkyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an alkoxy group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an alkenyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an aryl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an hetero ring group including O, N or S as a heteroatom, which is substituted or unsubstituted with one or more substituent groups selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a carbazolyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a fluorenyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an aryloxy group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an arylthio group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an alkoxycarbonyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a hydroxyl group; a carboxyl group; a nitrile group; a nitro group; a halogen group; —N(R')(R''); a nitrile group; a nitro group; a halogen group; —CO—N(R')(R''); and —COO—R', and said $R_1$ and $R_2$ may form an aliphatic or hetero condensation ring in conjunction with adjacent groups, and it is preferable that at least one of $R_3$ to $R_9$ is selected from the group consisting of deuterium; an alkenyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an hetero ring group including O, N or S as a heteroatom, which is substituted or unsubstituted with one or more substituent groups selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a carbazolyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a fluorenyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a nitrile group; —CO—N(R')(R''); and COO—R', and said $R_3$ to $R_9$ may form an aliphatic or hetero condensation ring in conjunct ion with adjacent groups, and the remains of $R_3$ to $R_9$ are selected from hydrogen or deuterium.

In addition, it is more preferable that $R_1$ and $R_2$ are each independently an aryl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; or an hetero ring group including O, N or S as a heteroatom, which is substituted or unsubstituted with one or more substituent groups selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group.

In addition, it is most preferable that $R_1$ and $R_2$ are each independently any one of the following groups, but is not limited thereto.

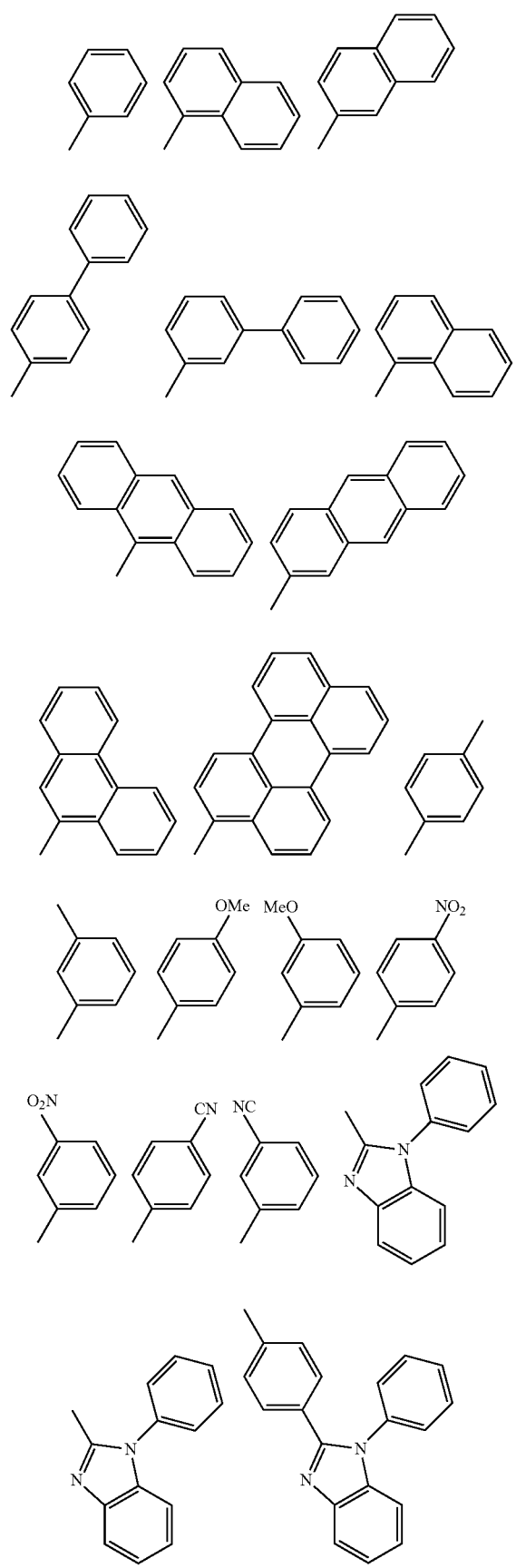

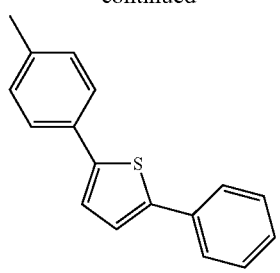

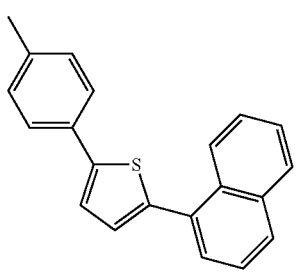

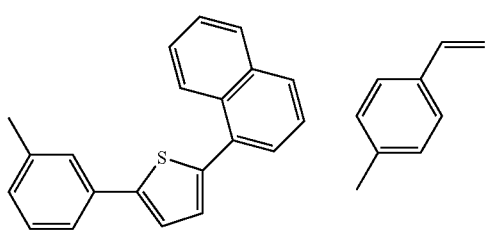

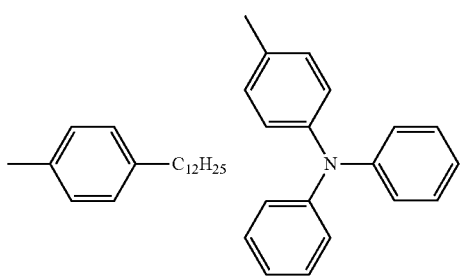

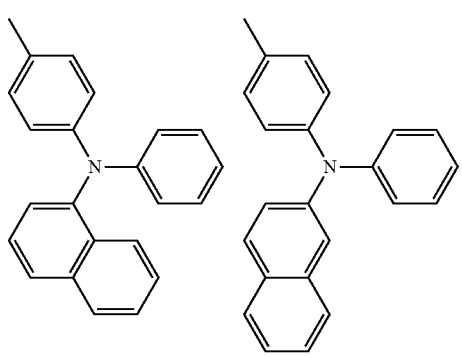

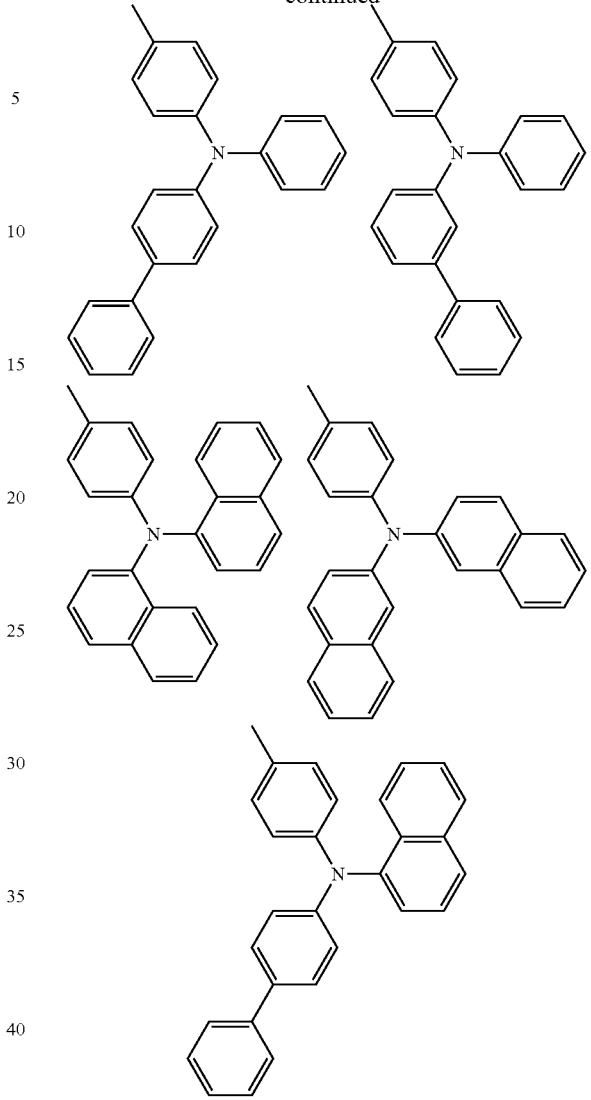

In $R_1$ to $R_9$ of Formula 1, the number of carbon atoms of the alkyl group, the alkoxy group, and the alkenyl group is not particularly limited, but it is preferable that it is in the range of 1 to 20.

The length of the alkyl group that is included in the compound does not affect the conjugation length of the compound, but may auxiliarily affect an application method of the compound to the organic light emitting device, for example, the application of a vacuum deposition method or a solution coating method.

Illustrative, but non-limiting, examples of the aryl group of $R_1$ to $R_9$ of Formula 1 include monocyclic aromatic rings, such as a phenyl group, a biphenyl group, a terphenyl group, and a stilbene group, and multicyclic aromatic rings, such as a naphthyl group, an anthracenyl group, a phenanthrene group, a pyrenyl group, and a perylenyl group.

Illustrative, but non-limiting, examples of the hetero ring group of $R_1$ to $R_9$ of Formula 1 include a thiophenyl group, a furan group, a pyrrolyl group, an imidazolyl group, a thiazolyl group, an oxazolyl group, an oxadiazolyl group, a triazolyl group, a pyridyl group, a pyradazine group, a quinolinyl group, an isoquinoline group, and an acridyl group.

Preferably, the compound of Formula 1 may be a compound that is represented by the following Formulas.

[Formula 2]
[Formula 3]
[Formula 4]
[Formula 5]
[Formula 6]
[Formula 7]
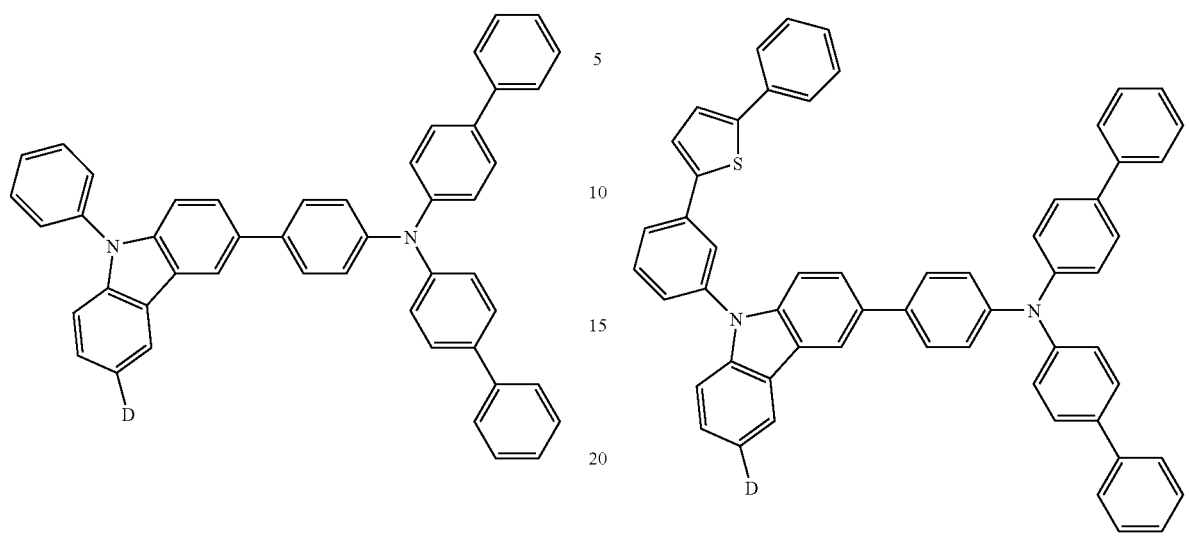
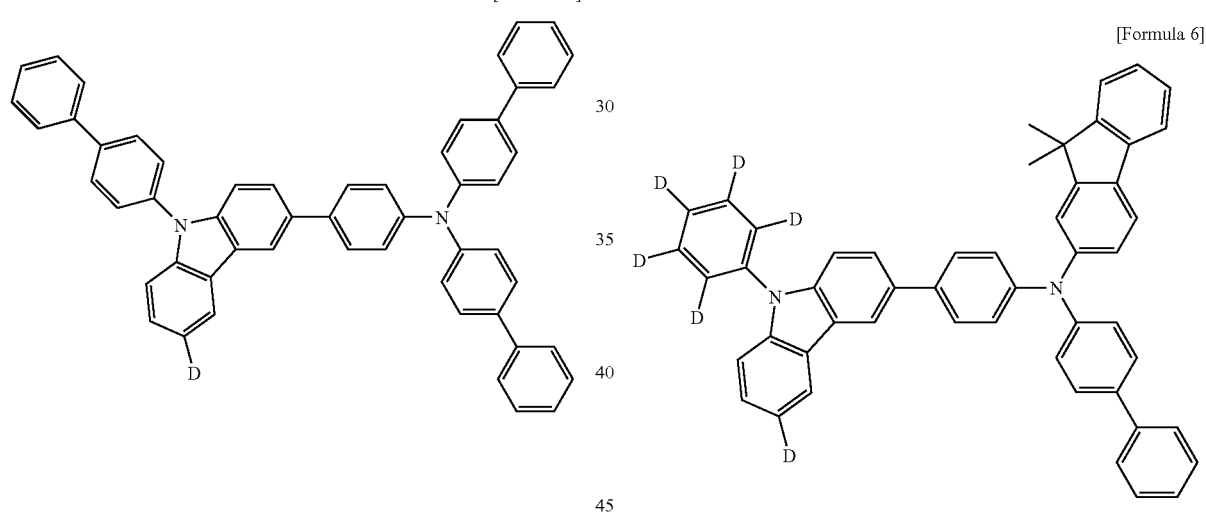
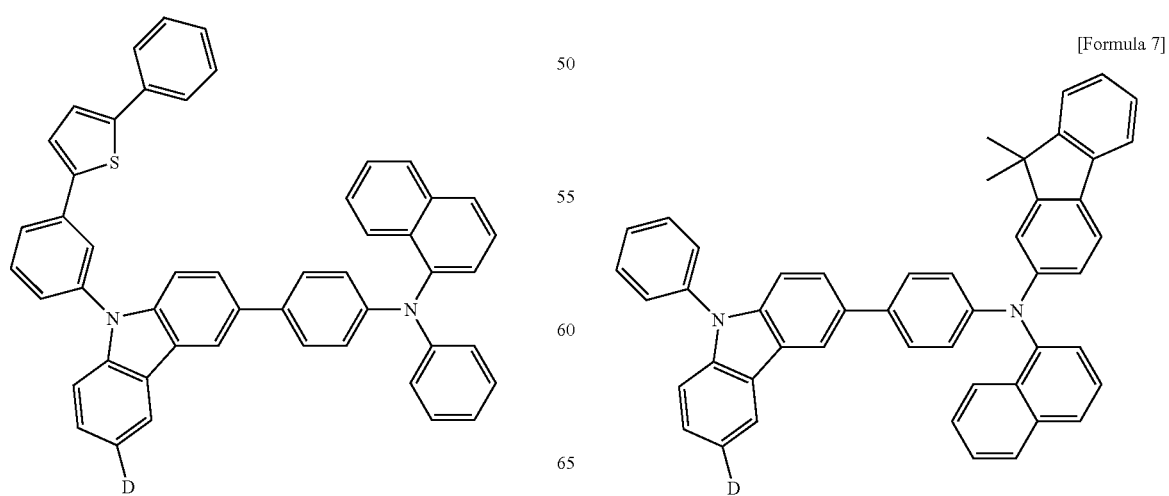

[Formula 8]
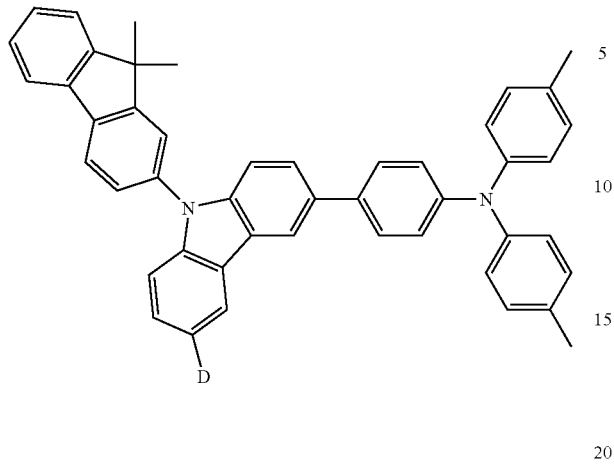
[Formula 9]
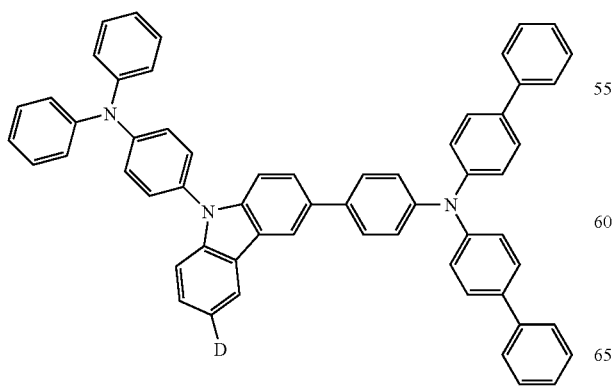
[Formula 10]
[Formula 11]
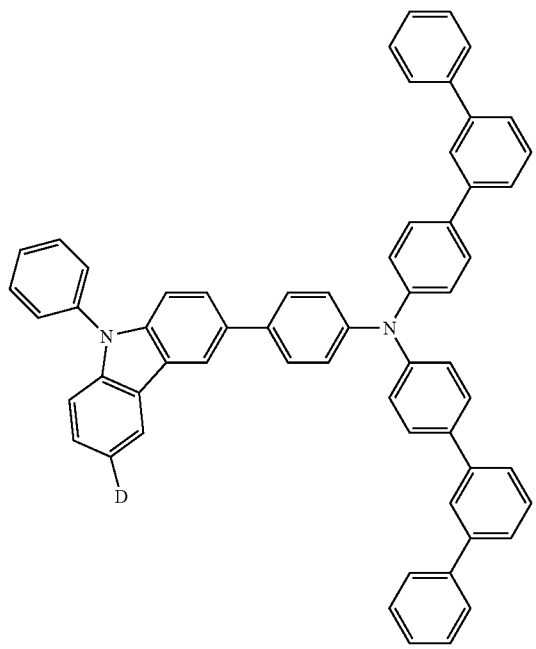
[Formula 12]
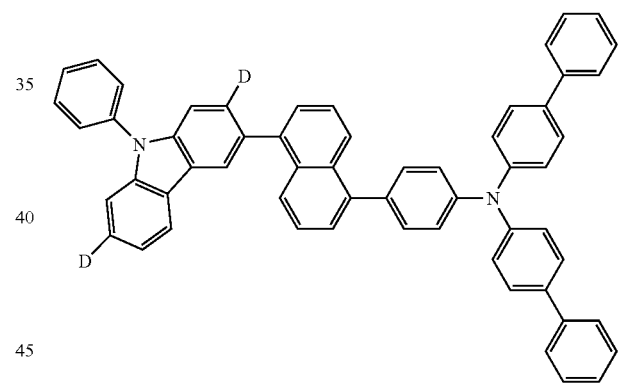
[Formula 13]
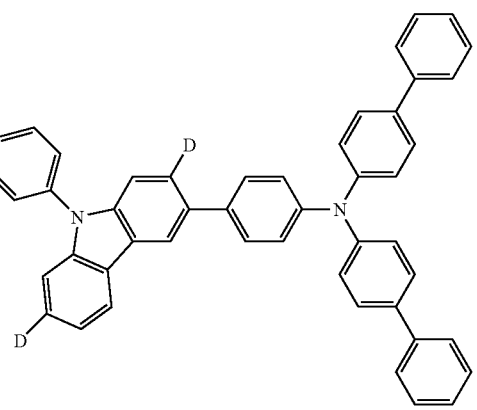

[Formula 14]
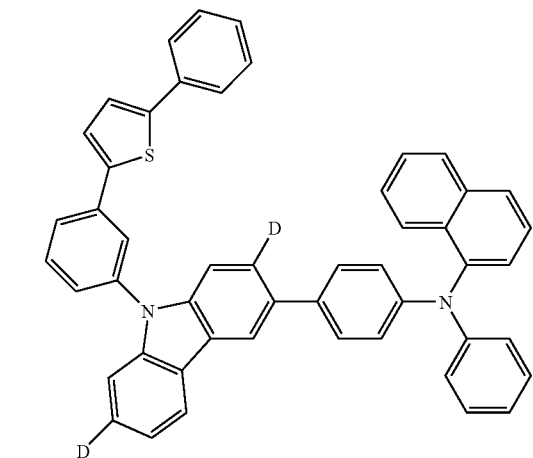
[Formula 15]
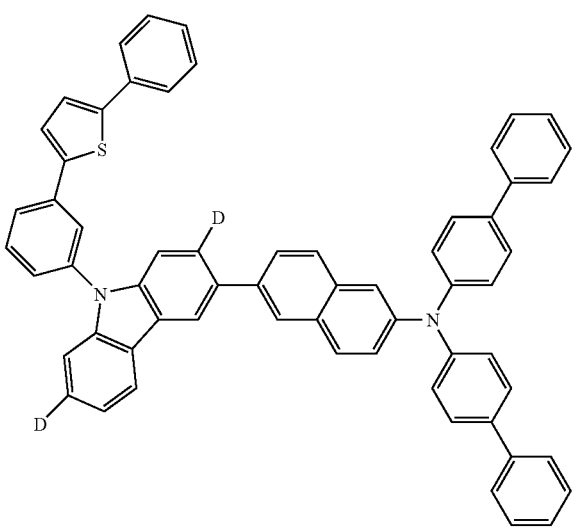
[Formula 16]
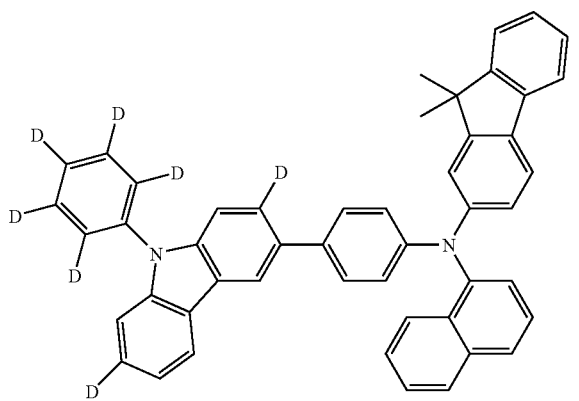
[Formula 17]
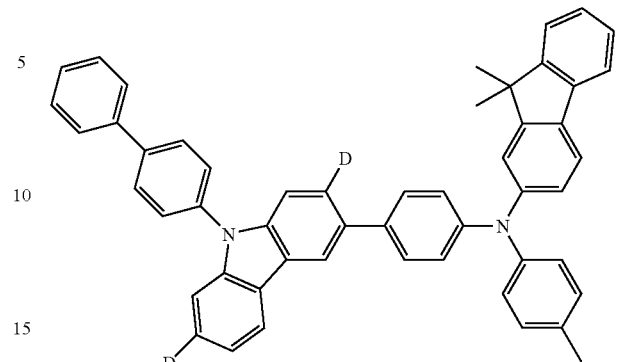
[Formula 18]
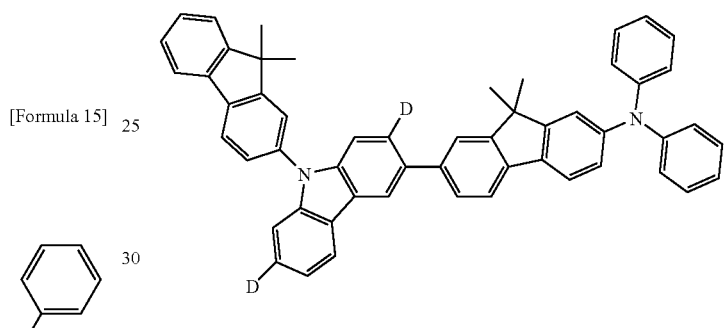
[Formula 19]
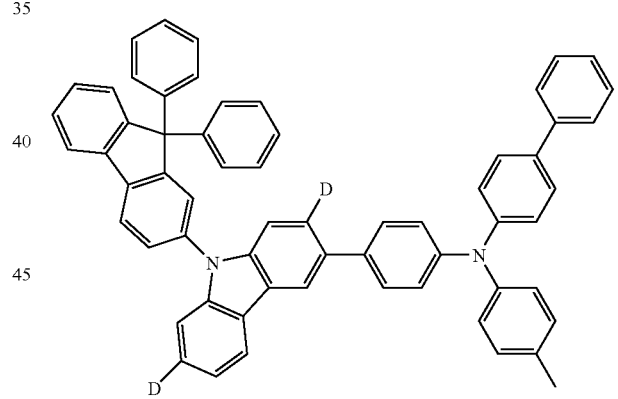
[Formula 20]
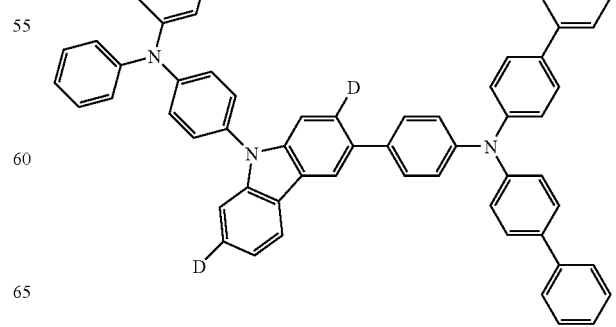

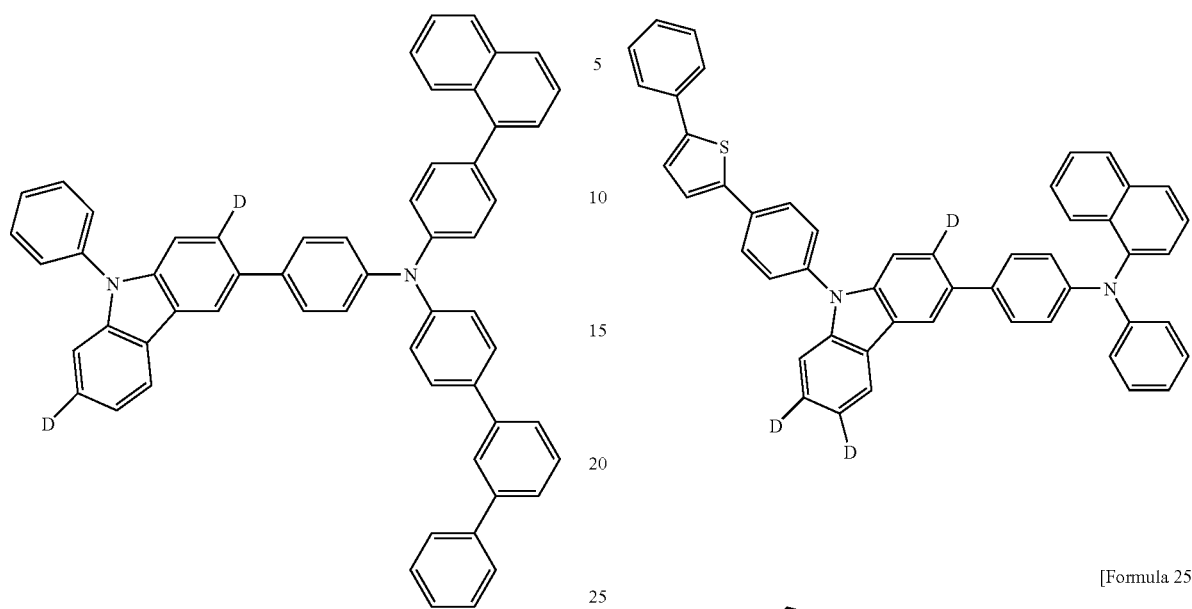
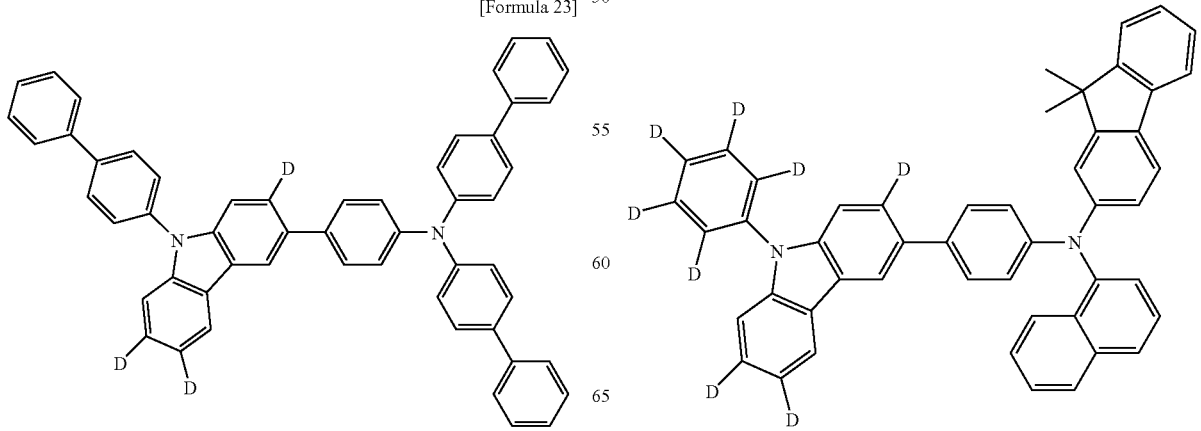

[Formula 27]
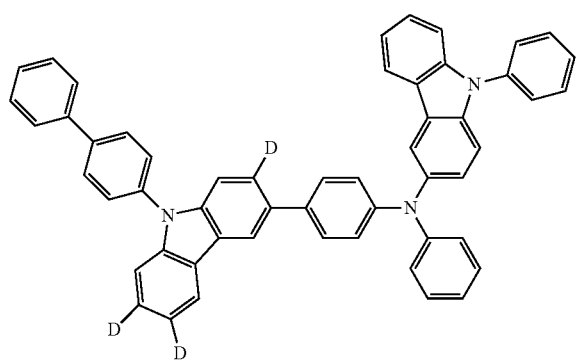
[Formula 28]
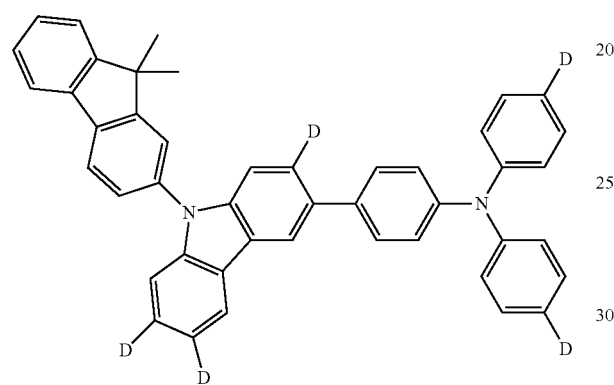
[Formula 29]
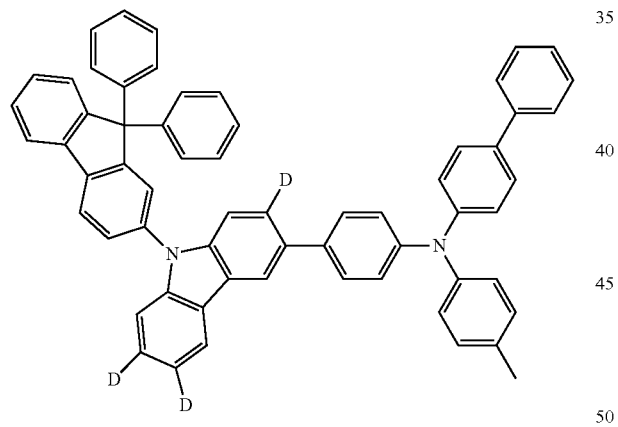
[Formula 30]
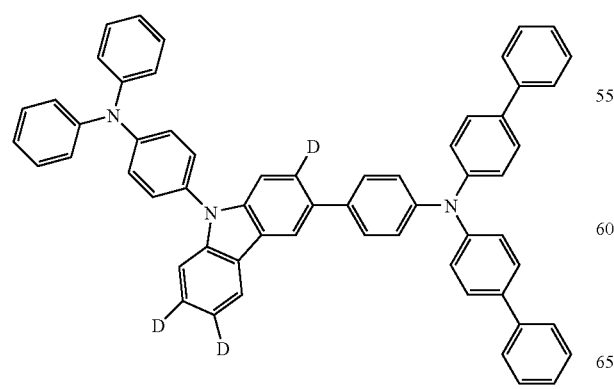
[Formula 31]
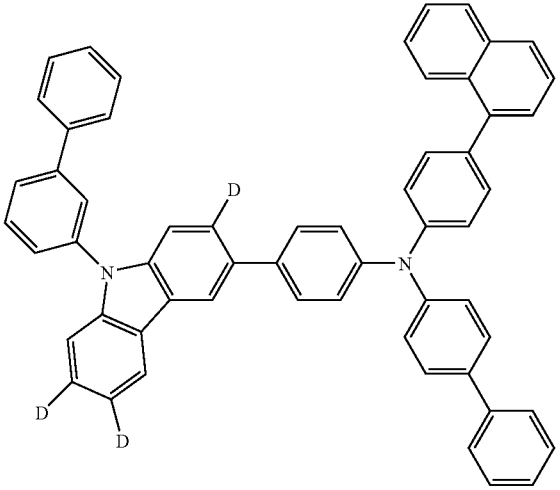
[Formula 32]
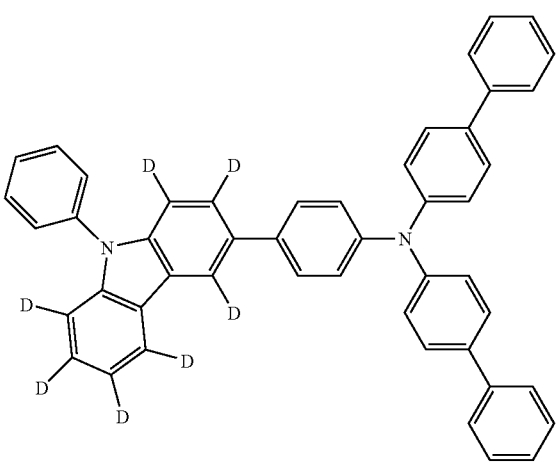
[Formula 33]
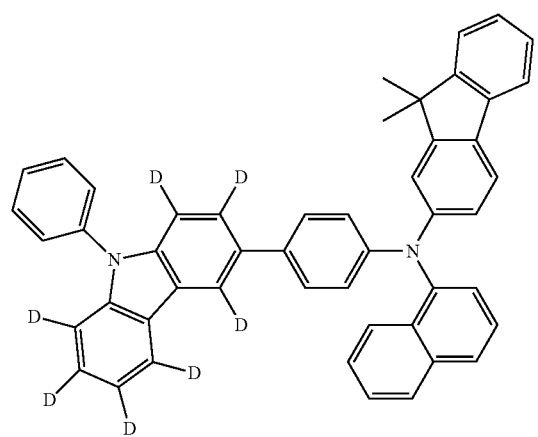

[Formula 34]
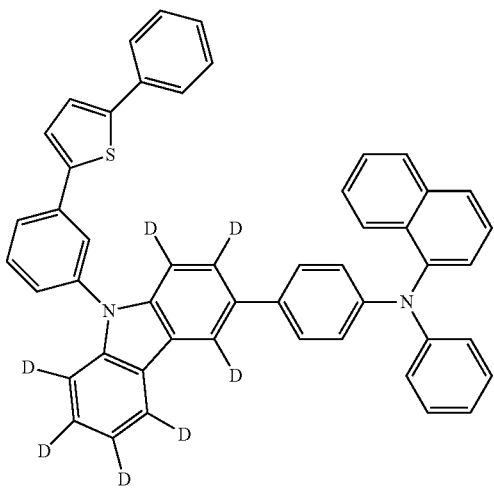
[Formula 35]
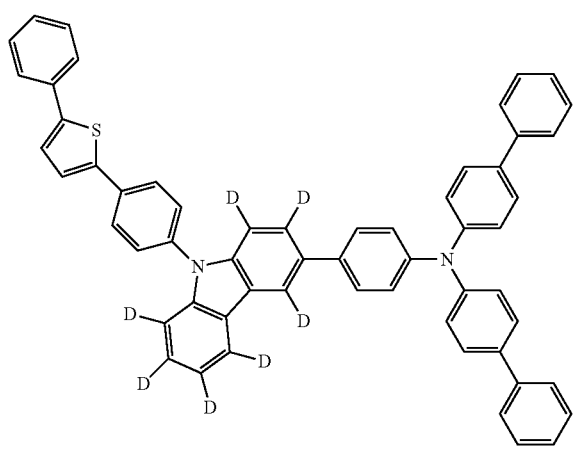
[Formula 36]
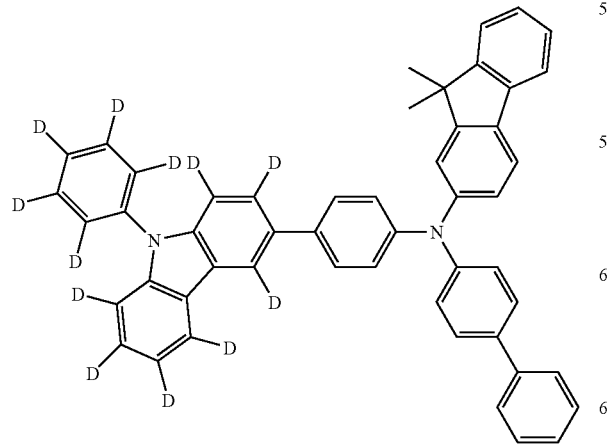
[Formula 37]
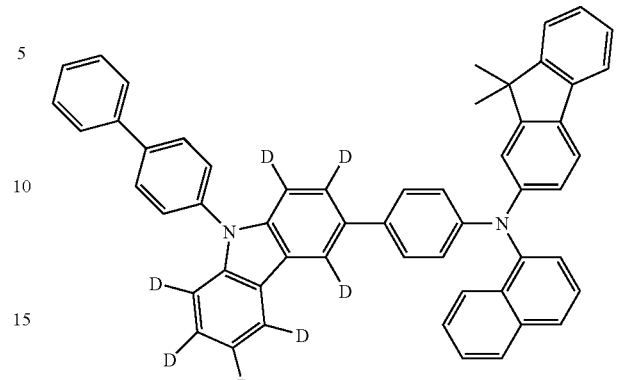
[Formula 38]
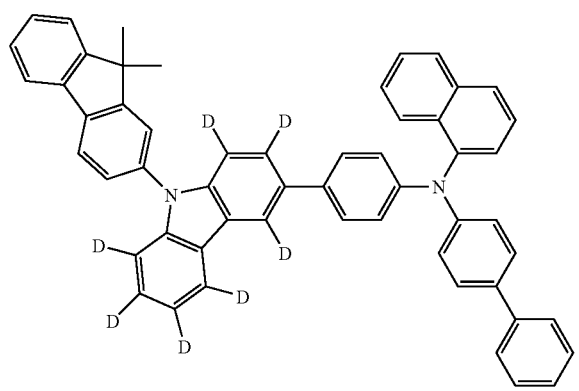
[Formula 39]
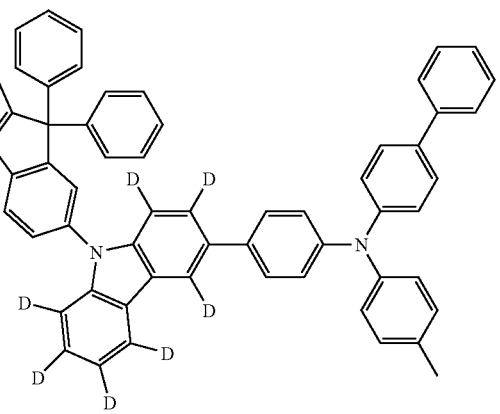
[Formula 40]
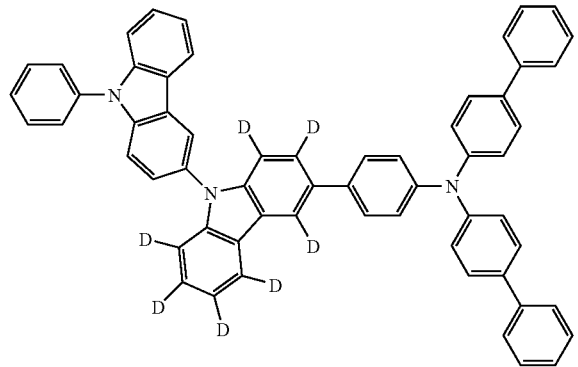

[Formula 41]

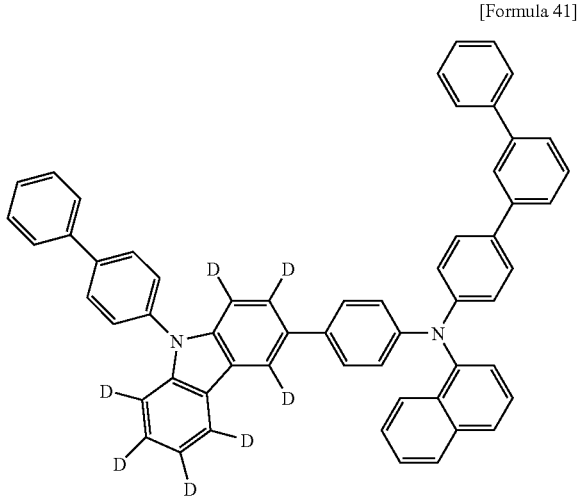

As shown in Formula 1, the compound of Formula 1 may have a property that is required when it is used as an organic material layer used in an organic light emitting device by using a structure in which carbazole is substituted with arylene and the like as a core structure and introducing various substituents, particularly, deuterium.

The conjugation length of the compound has a close relationship with an energy band gap. In detail, the energy band gap is reduced as the conjugation length of the compound increases. As described above, since a conjugation structure is limited in the core structure of the compound of Formula 1, the core structure has a large energy band gap.

As described above, in the present invention, various substituent groups are introduced to $R_1$ to $R_9$ and X positions of the core structure having the large energy band gap so as to produce compounds having various energy band gaps. Generally, it is easy to control an energy band gap by introducing substituent groups into a core structure having a large energy band gap, but it is difficult to significantly control the energy band gap by introducing substituent groups into a core structure having a small energy band gap. Furthermore, in the present invention, it is possible to control HOMO and LUMO energy levels of the compound by introducing various substituent groups into $R_1$ to $R_9$ and X of the core structure.

Additionally, by introducing various substituent groups into the core structure, compounds having intrinsic characteristics of the substituent groups may be obtained. For example, substituent groups, which are frequently applied to hole injection layer material, hole transport layer material, light emitting layer material, and electron transport layer materials during the production of the organic light emitting device, are introduced into the core structure so as to produce substances capable of satisfying the requirements of each organic material layer.

Since the core structure of the compound of Formula 1 includes the amine structure, it has an energy level suitable for the hole injection and/or hole transport materials in the organic light emitting device. In the present invention, the compound having the proper energy level is selected depending on the substituent group among the compounds represented by Formula 1 to be used in the organic light emitting device, thereby it is possible to realize a device having a low driving voltage and a high light efficiency.

Furthermore, various substituent groups, in particular, hydrogen or deuterium, are introduced into the core structure so as to precisely control the energy band gap, and to improve interfacial characteristics with organic materials, thereby apply the compound to various fields.

Meanwhile, since the compound of Formula 1 has a high glass transition temperature (Tg), it has excellent thermal stability. Such increase in thermal stability is an important factor providing driving stability to the device.

Furthermore, the compound of Formula 1 may be used to form the organic material layer using a vacuum deposition process or a solution coating process during the production of the organic light emitting device. In connection with this, illustrative, but non-limiting, examples of the solution coating process include a spin coating process, a dip coating process, an inkjet printing process, a screen printing process, a spray process, and a roll coating process.

The organic light emitting device of the present invention may be produced using known materials through a known process, modified only in that at least one layer of organic material layer(s) include the compound of the present invention, that is, the compound of Formula 1.

The organic material layer(s) of the organic light emitting device according to the present invention may have a single layer structure, or alternatively, a multilayered structure in which at least two organic material layers are layered. For example, the organic light emitting device of the present invention may comprise a hole injection layer, a hole transport layer, alight emitting layer, an electron transport layer, and an electron injection layer as the organic material layer(s). However, the structure of the organic light emitting device is not limited to this, but may comprise a smaller number of organic material layers.

Furthermore, the organic light emitting device of the present invention may be produced, for example, by sequentially layering a first electrode, organic material layer(s), and a second electrode on a substrate. In connection with this, a physical vapor deposition (PVD) method, such as a sputtering method or an e-beam evaporation method, may be used, but the method is not limited to these.

Mode for Invention

A better understanding of a method of manufacturing an compound represented by Formula 1 and the manufacturing of an organic light emitting device using the same may be obtained in light of the following Examples which are set forth to illustrate, but are not to be construed to limit the present invention.

EXAMPLE 1

Manufacturing of the Compound Represented by Formula 2

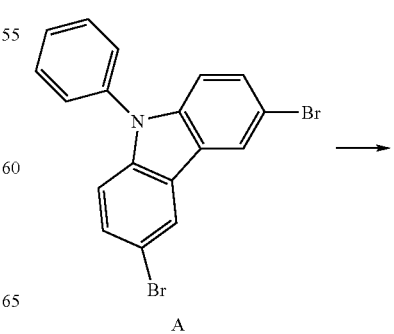

-continued

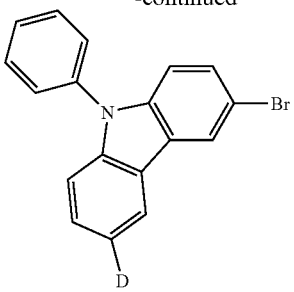

B

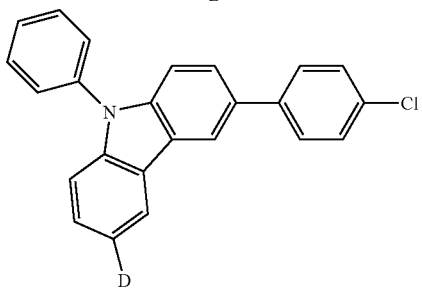

C

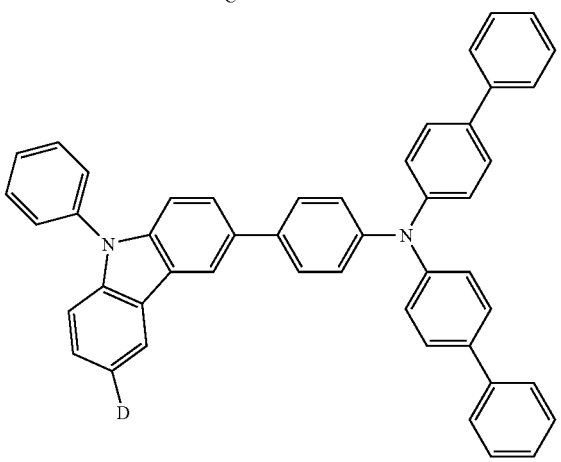

Formula 2

EXAMPLE 1-1

Manufacturing of the Compound A

N-phenylcarbazole (27 g, 111 mmol) was dissolved in chloroform (200 mL), N-bromosuccinimide (39.5 g, 222 mmol) was added thereto, and they were agitated for 5 hours at normal temperature. Distilled water was put into the reaction solution and the organic layer was extracted. It was dried by using anhydrous magnesium sulfate, distilled under the reduced pressure, and recrystallized by using tetrahydrofuran and ethanol to obtain a compound A (39 g, yield 88%). MS: $[M+H]^+=401$

EXAMPLE 1-2

Manufacturing of the Compound B

The compound A (30 g, 74.8 mmol) that was manufactured in Example 1-1 was dissolved in anhydrous tetrahydrofuran (200 ml), n-butyl lithium (2.5M hexane solution, 36 ml, 89.8 mmol) was added dropwise at −78° C., and after 1 hour, heavy water (2.24 g, 112 mmol) was put thereinto. After it was heated to normal temperature, water (50 ml) was put thereinto, it was agitated, and the organic layer was separated. The organic layer was dried by using anhydrous magnesium sulfate, filtered, and distilled under the reduced pressure. It was recrystallized by using hexane to obtain a compound B (12 g, yield 50%). MS: $[M+H]^+=323$

EXAMPLE 1-3

Manufacturing of the Compound C

After the compound B (12 g, 37.2 mmol) that was manufactured in Example 1-2 and 4-chlorophenyl boronic acid (6.3 g, 40 mmol) were dissolved in tetrahydrofuran (50 ml), tetrakis(triphenylphosphine)palladium (0.86 g, 0.74 mmol) and 2N potassium carbonate aqueous solution were put thereinto and refluxed for 12 hours. After the reaction was finished, it was cooled to normal temperature, and the organic layer was separated and dried by using anhydrous magnesium sulfate. After it was distilled under the reduced pressure, it was recrystallized by using ethanol to obtain a compound C (11 g, yield 84%). MS: $[M+H]^+=354$

EXAMPLE 1-4

Manufacturing of the Compound 2

The compound C (4 g, 11.3 mmol) that was manufactured in Example 1-3 and bis(4-biphenylyl)amine (4.18 g, 13 mmol) were dissolved in xylene (100 ml), sodium-tertiary-butoxide (1.4 g, 14.7 mmol) and bis(tri tertiary-butyl phosphine)palladium (0.11 g, 0.23 mmol) were added thereto, and they were refluxed for 5 hours under a nitrogen atmosphere. After the reaction was finished, it was cooled to normal temperature, an acidic white clay was put, and then agitated. After it was filtered, it was distilled under the reduced pressure and subjected to column purification by using a hexane/tetrahydrofuran=10/1 solvent to obtain Formula 2 (3.9 g, yield 54%). MS: $[M+H]^+=639$

EXAMPLE 2

Manufacturing of the Compound Represented by Formula 3

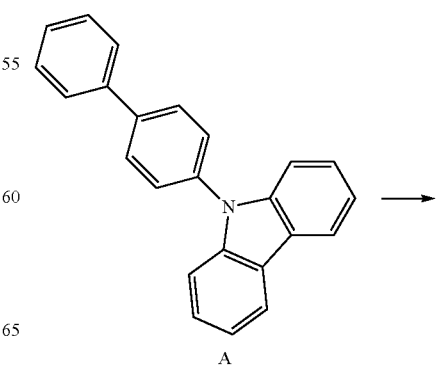

A

-continued

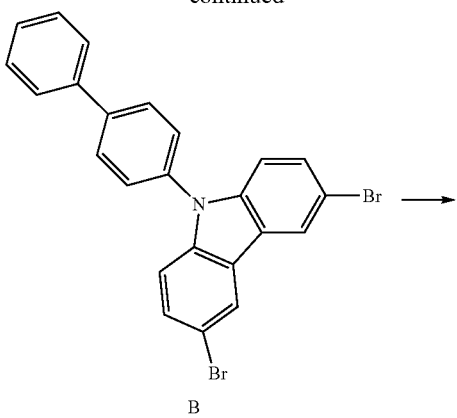
B

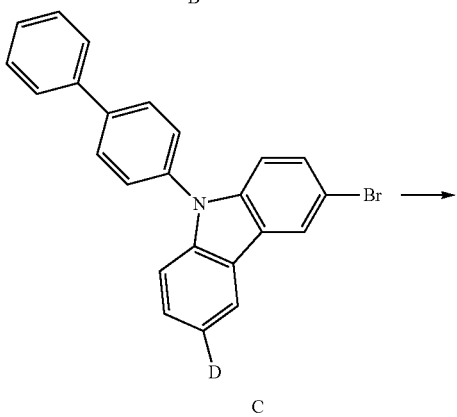
C

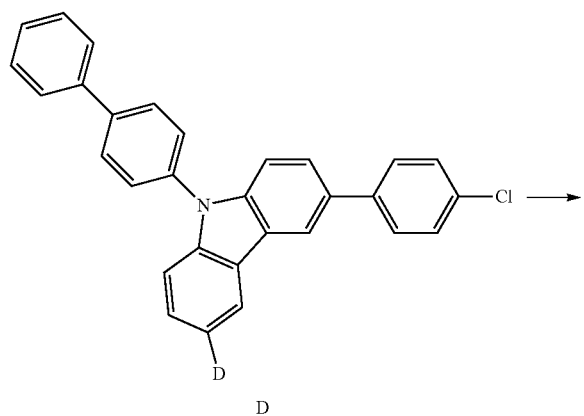
D

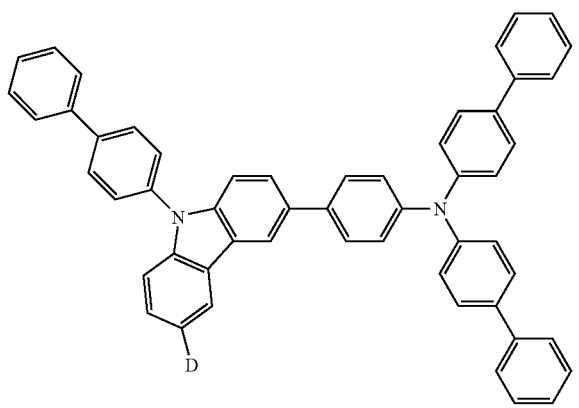
Formula 3

EXAMPLE 2-1

Manufacturing of the Compound A

Carbazole (20 g, 119.6 mmol) and 4-bromobiphenyl (28 g, 120 mmol) were dissolved in xylene (400 ml), sodium-tertiary-butoxide (15 g, 156 mmol) and bis (tri tertiary-butyl phosphine)palladium (0.6 g, 1.2 mmol) were added thereto, and they were refluxed for 12 hours under a nitrogen atmosphere. After the reaction was finished, it was cooled to normal temperature, and the manufactured solid was filtered. It was sequentially washed by using toluene and ethanol, and dried to obtain a compound A (31.8 g, yield 83%). MS: $[M+H]^+=320$

EXAMPLE 2-2

Manufacturing of the Compound B

The compound A (30 g, 93.9 mmol) that was manufactured in Example 2-1 was dissolved in chloroform (500 mL), N-bromosuccinimide (35.6 g, 200 mmol) was added thereto, and they were agitated for 5 hours at normal temperature. Distilled water was put into the reaction solution and the organic layer was extracted. It was distilled under the reduced pressure, and recrystallized by using tetrahydrofuran and ethanol to obtain a compound B (39.4 g, yield 88%). MS: $[M+H]^+=478$

EXAMPLE 2-3

Manufacturing of the Compound C

The compound B (35 g, 73.3 mmol) that was manufactured in Example 2-2 was dissolved in anhydrous tetrahydrofuran (500 ml), n-butyl lithium (2.5M hexane solution, 29.3 ml, 73.3 mmol) was added dropwise at −78° C., and after 1 hour, heavy water (2.24 g, 112 mmol) was put thereinto. After it was heated to normal temperature, water (50 ml) was put thereinto, it was agitated, and the organic layer was separated. The organic layer was dried by using anhydrous magnesium sulfate, filtered, and distilled under the reduced pressure. It was recrystallized by using hexane to obtain a compound C (14 g, yield 48%). MS. $[M+H]^+=400$

EXAMPLE 2-4

Manufacturing of the Compound D

After the compound C (14 g, 35 mmol) that was manufactured in Example 2-3 and 4-chlorophenyl boronic acid (5.9 g, 38 mmol) were dissolved in tetrahydrofuran (150 ml), tetrakis (triphenylphosphine)palladium (0.81 g, 0.7 mmol) and 2N potassium carbonate aqueous solution were put thereinto and refluxed for 12 hours. After the reaction was finished, it was cooled to normal temperature, and the manufactured solid was filtered. It was sequentially washed by using water and ethanol and dried to obtain a compound D (12.8 g, yield 85%)). MS: $[M+H]^+=431$

EXAMPLE 2-5

Manufacturing of the Formula 3

The compound D (10 g, 23.2 mmol) that was manufactured in Example 2-4 and bis(4-biphenylyl)amine (7.7 g, 24 mmol) were dissolved in xylene in an amount of 100 ml, sodium-tertiary-butoxide (2.9 g, 30 mmol) and bis(tri tertiary-butyl phosphine)palladium (0.11 g, 0.23 mmol) were added thereto, and they were refluxed for 5 hours under a nitrogen atmosphere. After the reaction was finished, it was cooled to normal temperature, and the manufactured solid was filtered. It was sequentially washed by using toluene and ethanol, dissolved in chloroform, an acidic white clay was put thereinto, and they were agitated. After it was filtered, distilled under the reduced pressure, and recrystallized by using tetrahydrofuran and ethanol to obtain Formula 3 (10.1 g, yield 61%). MS: $[M+H]^+=716$

EXAMPLE 3

Manufacturing of the Compound Represented by Formula 4

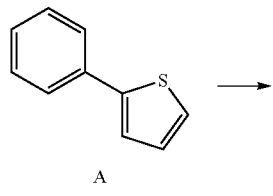

A

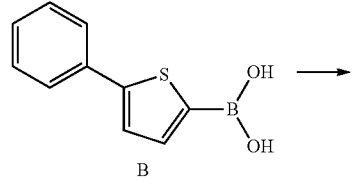

B

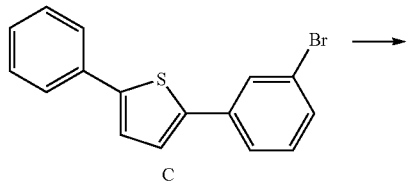

C

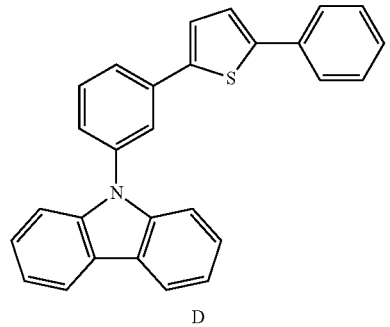

D

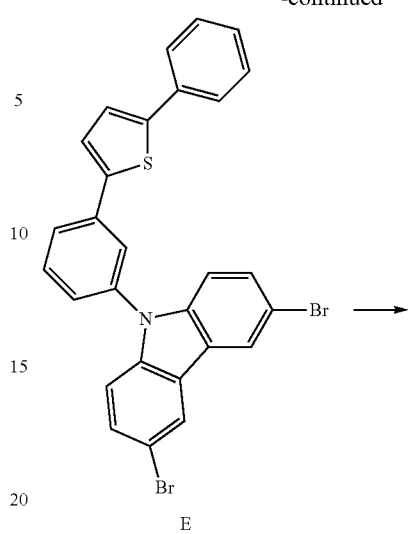

E

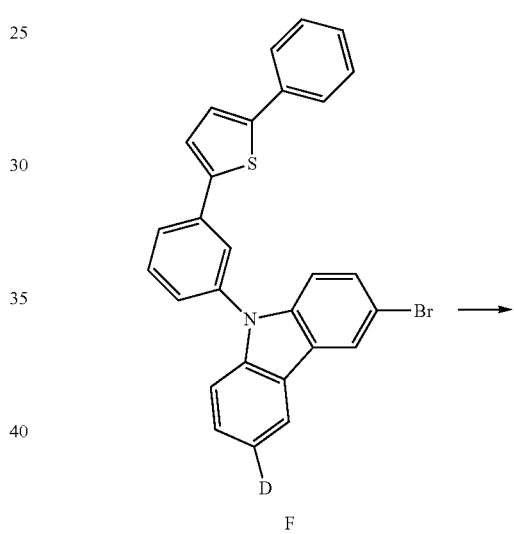

F

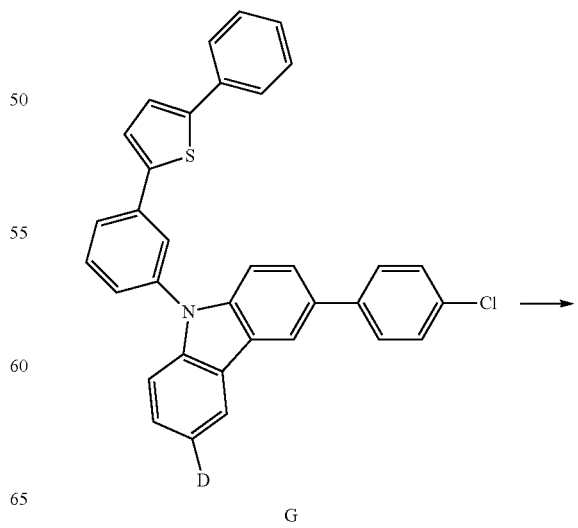

G

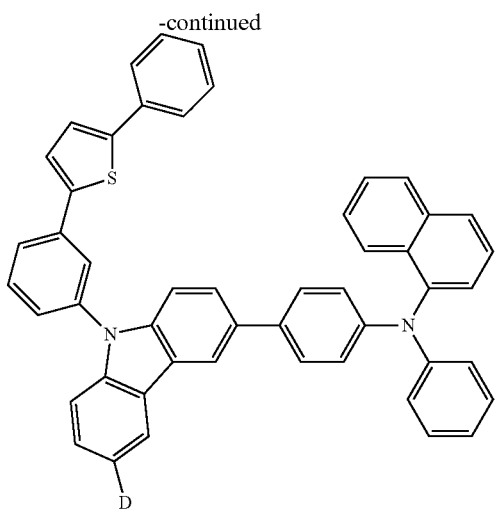

Formula 4

EXAMPLE 3-1

Manufacturing of the Compound A

After 2-bromothiopene (20 g, 122.7 mmol) and phenyl boronate (15.9 g, 130.4 mmol) were dissolved in tetrahydrofuran (150 ml), tetrakis(triphenylphosphine)palladium (2.9 g, 2.5 mmol) and 2N potassium carbonate aqueous solution were put thereinto and refluxed for 12 hours. After the reaction was finished, it was cooled to normal temperature, and the organic layer was separated and dried by using anhydrous magnesium sulfate. After it was distilled under the reduced pressure, it was recrystallized by using hexane at 0° C. to obtain a compound A (17.2 g, yield 87%). MS: $[M+H]^+=161$

EXAMPLE 3-2

Manufacturing of the Compound B

The compound A (15 g, 93.6 mmol) that was manufactured in Example 3-1 was dissolved in anhydrous tetrahydrofuran (300 ml), n-butyl lithium (2.5M hexane solution, 41.2 ml, 103 mmol) was added dropwise at −78° C., and after 1 hour, trimethyl borate (11.4 g, 110 mmol) was put thereinto. After 1 hour, 1N hydrogen chloride aqueous solution was put thereinto, and it was heated to normal temperature. After the organic layer was separated, it was dried by using anhydrous magnesium sulfate, and distilled under the reduced pressure. It was recrystallized by using ethyl ether and hexane to obtain a compound B (13 g, yield 68%). MS: $[M+H]^+=205$

EXAMPLE 3-3

Manufacturing of the Compound C

After the compound B (13 g, 63.7 mmol) that was manufactured in Example 3-2 and 1-bromo-3-iodobenzene (19.8 g, 70 mmol) were dissolved in tetrahydrofuran (200 ml), tetrakis(triphenylphosphine)palladium (1.5 g, 1.3 mmol) and 2N potassium carbonate aqueous solution were put thereinto and refluxed for 12 hours. After the reaction was finished, it was cooled to normal temperature, and the organic layer was separated and dried by using anhydrous magnesium sulfate. After it was distilled under the reduced pressure, it was recrystallized by using tetrahydrofuran and ethanol to obtain a compound C (14.8 g, yield 74%). MS: $[M+H]^+=316$

EXAMPLE 3-4

Manufacturing of the Compound D

Carbazole (5 g, 29.9 mmol) and the compound C (9.4 g, 29.9 mmol) that was manufactured in Example 3-3 were suspended in xylene (100 ml), sodium-tertiary-butoxide (3.7 g, 38 mmol) and bis (tri tertiary-butyl phosphine)palladium (0.15 g, 0.3 mmol) were added thereto, and they were refluxed for 12 hours under a nitrogen atmosphere. After the reaction was finished, it was cooled to normal temperature, and the manufactured solid was filtered. It was sequentially washed by using toluene and ethanol, and dried to obtain a compound D (9.5 g, yield 79%). MS: $[M+H]^+=402$

EXAMPLE 3-5

Manufacturing of the Compound E

The compound D (9 g, 22.4 mmol) that was manufactured in Example 3-4 was dissolved in chloroform (100 mL), N-bromosuccinimide (8 g, 45 mmol) was added thereto, and they were agitated for 5 hours at normal temperature. Distilled water was put into the reaction solution and the organic layer was extracted. It was distilled under the reduced pressure, and recrystallized by using tetrahydrofuran and ethanol to obtain a compound E (11.2 g, yield 89%). MS: $[M+H]^+=560$

EXAMPLE 3-6

Manufacturing of the Compound F

The compound E (11 g, 19.7 mmol) that was manufactured in Example 3-5 was dissolved in anhydrous tetrahydrofuran (200 ml), n-butyl lithium (2.5M hexane solution, 7.9 ml, 19.7 mmol) was added dropwise at −78° C., and after 1 hour, heavy water (0.6 g, 30 mmol) was put thereinto. After it was heated to normal temperature, water (50 ml) was put thereinto, it was agitated, and the organic layer was separated. The organic layer was dried by using anhydrous magnesium sulfate, filtered, and distilled under the reduced pressure. It was recrystallized by using tetrahydrofuran and ethanol to obtain a compound F (4.9 g, yield 52%). MS: $[M+H]^+=482$

EXAMPLE 3-7

Manufacturing of the Compound G

After the compound F (4.5 g, 9.3 mmol) that was manufactured in Example 3-6 and 4-chlorophenyl boronic acid (1.7 g, 11 mmol) were dissolved in tetrahydrofuran (100 ml), tetrakis(triphenylphosphine)palladium (0.22 g, 0.19 mmol) and 2N potassium carbonate aqueous solution were put thereinto and refluxed for 12 hours. After the reaction was finished, it was cooled to normal temperature, and the organic layer was separated and dried by using anhydrous magnesium sulfate and filtered. After it was distilled under the reduced pressure, it was recrystallized by using tetrahydrofuran and ethanol to obtain a compound G (3.8 g, yield 79%). MS: $[M+H]^+=513$

EXAMPLE 3-8

Manufacturing of the Formula 4

The compound G (3.5 g, 6.8 mmol) that was manufactured in Example 3-7 and N-phenyl-1-naphthyl amine (1.6 g, 7.3 mmol) were dissolved in xylene (80 ml), sodium-tertiary-butoxide (0.85 g, 8.8 mmol) and bis(tri tertiary-butyl phosphine)palladium (0.04 g, 0.08 mmol) were added thereto, and they were refluxed for 5 hours under a nitrogen atmosphere. After the reaction was finished, it was cooled to normal temperature, and an acidic white clay was put thereinto, and they were agitated. After it was filtered, distilled under the reduced pressure, and subjected to the column purification by using a hexane/tetrahydrofuran=7/1 solvent and ethanol to obtain Formula 4 (2.9 g, yield 61%). MS: [M+H]$^+$=696

EXAMPLE 4

Manufacturing of the Compound Represented by Formula 7

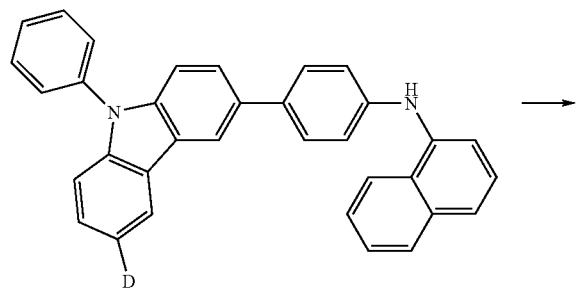

A

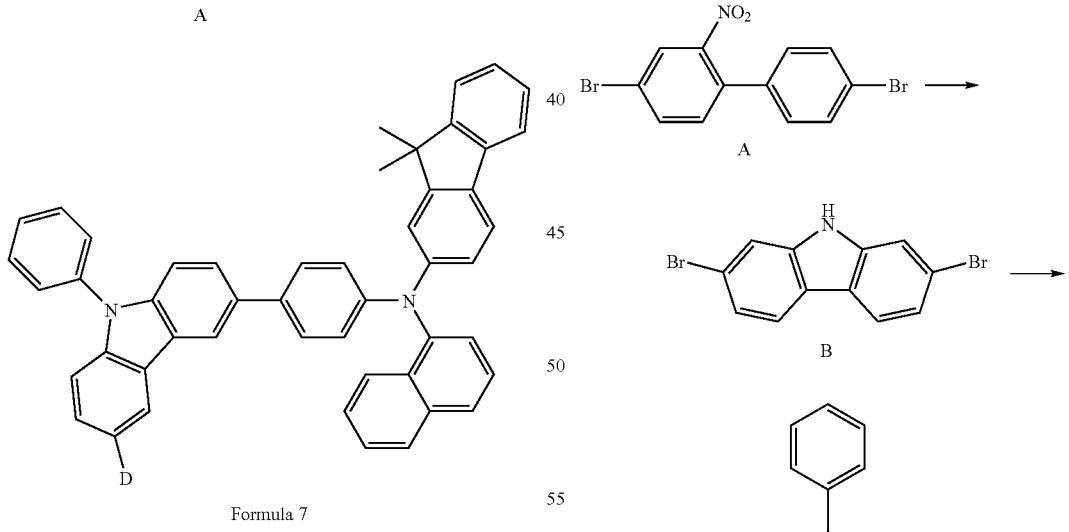

Formula 7

EXAMPLE 4-1

Manufacturing of the Compound A

The compound C (5 g, 14.1 mmol) that was manufactured in Example 1-3 and 1-aminonaphthalene (2 g, 14 mmol) were dissolved in toluene (80 ml), sodium-tertiary-butoxide (1.7 g, 18 mmol) and bis(tri tertiary-butyl phosphine)palladium (0.07 g, 0.14 mmol) were added thereto, and they were refluxed for 5 hours under a nitrogen atmosphere. After the reaction was finished, it was cooled to normal temperature, and an acidic white clay was put thereinto, and they were agitated. After it was filtered, distilled under the reduced pressure, and subjected to the column purification by using a hexane/tetrahydrofuran=10/1 solvent and ethanol to obtain a compound A (2.9 g, yield 61%). MS: [M+H]$^+$=462

EXAMPLE 4-2

Manufacturing of the Formula 7

The compound A (2.5 g, 5.4 mmol) that was manufactured in Example 4-1 and 2-bromo-9, 9-dimethylfluorene (1.6 g, 5.9 mmol) were dissolved in toluene (80 ml), sodium-tertiary-butoxide (0.67 g, 7 mmol) and bis(tri tertiary-butyl phosphine)palladium (0.03 g, 0.06 mmol) were added thereto, and they were refluxed for 5 hours under a nitrogen atmosphere. After the reaction was finished, it was cooled to normal temperature, and an acidic white clay was put thereinto, and they were agitated. After it was filtered, distilled under the reduced pressure, and subjected to the column purification by using a hexane/tetrahydrofuran=8/1 solvent to obtain a compound 7 (2.1 g, yield 59%). MS: [M+H]$^+$=654

EXAMPLE 5

Manufacturing of the Compound Represented by Formula 13

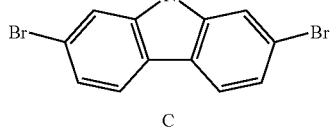

A

B

C

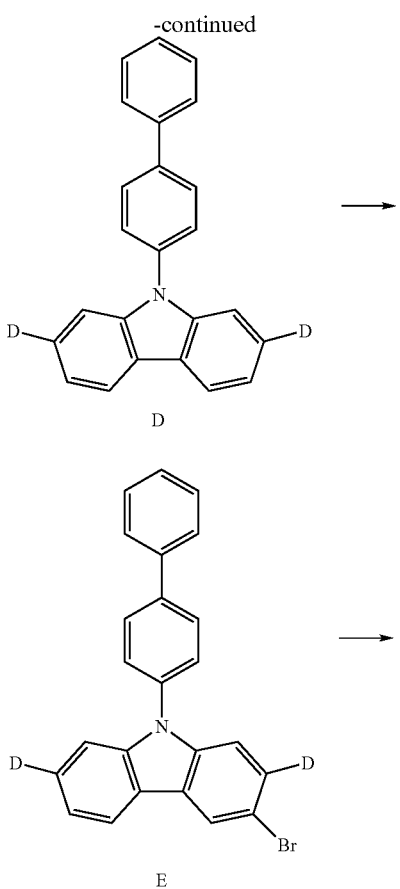

EXAMPLE 5-1

Manufacturing of the Compound A

Into the solution in which a nitric acid (40 ml) and an acetic acid (40 ml) were mixed with each other, 4,4'-dibromobiphenyl (18 g, 57.7 mmol) was slowly put while it was suspended in dichloromethane (50 ml) and an acetic acid (300 ml). After 18 hours, the reaction solution was poured into the sodium hydroxide aqueous solution to neutralize it, and it was extracted by using dichloromethane. The organic layer was dried by using anhydrous magnesium sulfate and distilled under the reduced pressure, recrystallized by using methanol to obtain a compound A (16.9 g, yield 82%). MS: [M+H]+= 358

EXAMPLE 5-2

Manufacturing of the Compound B

The compound A (16 g, 44.8 mmol) that was manufactured in Example 5-1 and triphenyl phosphine (29.4 g, 112 mmol) were mixed with each other, and it was refluxed while o-dichlorobenzene (100 ml) was put thereinto and agitated. After the reaction was finished, it was cooled to normal temperature and distilled under the reduced pressure. It was subjected to the column purification by using a ligroin/dichloromethane=3/1 solvent to obtain a compound B (10.6 g, yield 73%). MS: $[M+H]^+=326$

EXAMPLE 5-3

Manufacturing of the Compound C

The compound B (10 g, 30.7 mmol) that was manufactured in Example 5-2 and iodobiphenyl (11.2 g, 40 mmol), and potassium carbonate (8.3 g, 60 mmol) were suspended in dimethylacetamide (100 ml), copper (2 g, 31.5 mmol) was put thereinto, and they were refluxed for 12 hours under a nitrogen atmosphere. After the reaction was finished, it was cooled to normal temperature, and was filtered. The filtration solution was poured into water, extracted by using chloroform, and dried by using anhydrous magnesium sulfate. After it was distilled under the reduced pressure, it was subjected to the column purification by using a hexane/tetrahydrofuran=10/1 solvent to obtain a compound C (6.2 g, yield 42%). MS: $[M+H]^+=478$

EXAMPLE 5-4

Manufacturing of the Compound D

The compound C (6 g, 12.6 mmol) that was manufactured in Example 5-3 was dissolved in anhydrous tetrahydrofuran (100 ml), n-butyl lithium (2.5M hexane solution, 12.1 ml, 30.2 mmol) was added dropwise at −78° C., and after 1 hour, heavy water (1.1 g, 55 mmol) was put thereinto. After it was heated to normal temperature, water (30 ml) was put thereinto, it was agitated, and the organic layer was separated. The organic layer was dried by using anhydrous magnesium sulfate, filtered, and distilled under the reduced pressure. It was recrystallized by using tetrahydrofuran and ethanol to obtain a compound D (2.4 g, yield 59%). MS: $[M+H]^+=322$

EXAMPLE 5-5

Manufacturing of the Compound E

The compound D (2 g, 6.2 mmol) that was manufactured in Example 5-4 was dissolved in chloroform (60 mL), N-bromosuccinimide (1.1 g, 6.2 mmol) was added thereto, and they were agitated for 5 hours at normal temperature. Distilled water was put into the reaction solution and the organic layer was extracted. It was distilled under the reduced pressure, and recrystallized by using tetrahydrofuran and ethanol to obtain a compound E (1.8 g, yield 73%). MS: [M+H]⁺=401

EXAMPLE 5-6

Manufacturing of the Compound F

After the compound E (1.5 g, 3.7 mmol) that was manufactured in Example 5-5 and 4-chlorophenyl boronic acid (0.69 g, 4.4 mmol) were dissolved in tetrahydrofuran (70 ml), tetrakis(triphenylphosphine)palladium (0.09 g, 0.07 mmol) and 2N potassium carbonate aqueous solution were put thereinto and refluxed for 12 hours. After the reaction was finished, it was cooled to normal temperature, and the organic layer was separated and dried by using anhydrous magnesium sulfate. After it was distilled under the reduced pressure, it was recrystallized by using tetrahydrofuran and ethanol to obtain a compound F (1.1 g, yield 69%). MS: [M+H]⁺=432

EXAMPLE 5-7

Manufacturing of the Formula 13

The compound F (1.1 g, 2.5 mmol) that was manufactured in Example 5-6 and bis(4-biphenylyl)amine (0.87 g, 2.7 mmol) were dissolved in xylene (50 ml), sodium-tertiary-butoxide (0.32 g, 3.3 mmol) and bis(tri tertiary-butyl phosphine)palladium (0.02 g, 0.04 mmol) were added thereto, and they were refluxed for 5 hours under a nitrogen atmosphere. After the reaction was finished, it was cooled to normal temperature, an acidic white clay was put, and then agitated. After it was filtered, it was distilled under the reduced pressure and recrystallized by using tetrahydrofuran and ethanol to obtain Formula 13 (1.1 g, yield 61%). MS: [M+H]⁺=717

EXAMPLE 6

Manufacturing of the Compound Represented by Formula 17

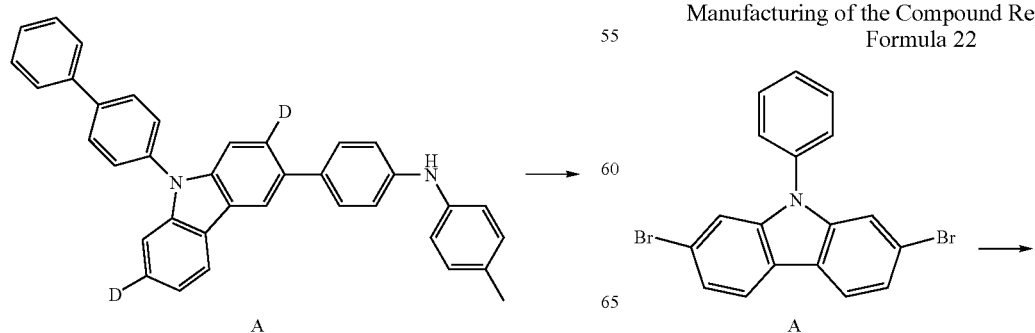

A

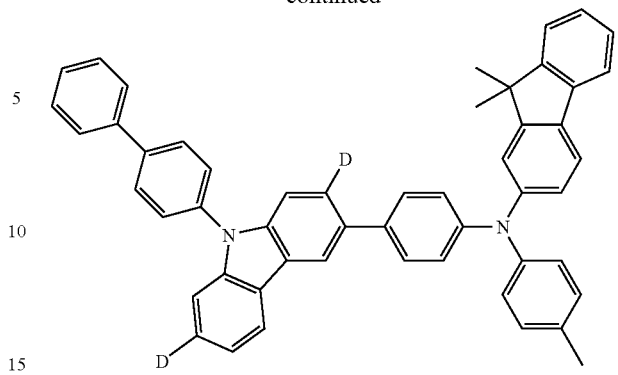

Formula 17

EXAMPLE 6-1

Manufacturing of the Compound A

The compound F (2 g, 4.6 mmol) that was manufactured in Example 5-6 and p-toluydine (0.59 g, 5.5 mmol) were dissolved in xylene (50 ml), sodium-tertiary-butoxide (0.58 g, 6 mmol) and bis(tri tertiary-butyl phosphine)palladium (0.02 g, 0.04 mmol) were added thereto, and they were refluxed for 5 hours under a nitrogen atmosphere. After the reaction was finished, it was cooled to normal temperature, an acidic white clay was put, and then agitated. After it was filtered, it was distilled under the reduced pressure and subjected to column purification by using a hexane/tetrahydrofuran=8/1 solvent to obtain the compound A (1.6 g, yield 69%). MS: [M+H]⁺=503

EXAMPLE 6-2

Manufacturing of the Formula 17

The compound A (1.5 g, 3 mmol) that was manufactured in Example 6-1 and 2-bromo-9,9-dimethylfluorene (0.9 g, 3.3 mmol) were dissolved in xylene (50 ml), sodium-tertiary-butoxide (0.37 g, 3.9 mmol) and bis(tri tertiary-butyl phosphine)palladium (0.02 g, 0.04 mmol) were added thereto, and they were refluxed for 5 hours under a nitrogen atmosphere. After the reaction was finished, it was cooled to normal temperature, an acidic white clay was put, and then agitated. After it was filtered, it was distilled under the reduced pressure and subjected to column purification by using a hexane/tetrahydrofuran=6/1 solvent to obtain Formula 17 (1.2 g, yield 58%). MS: [M+H]⁺=695

EXAMPLE 7

Manufacturing of the Compound Represented by Formula 22

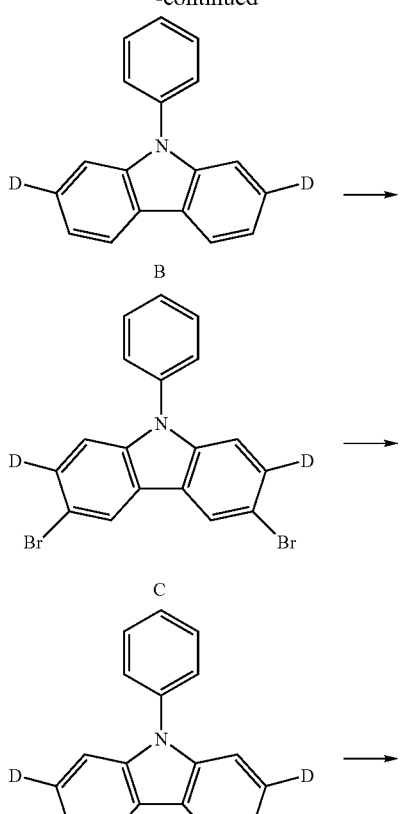

B

C

D

E

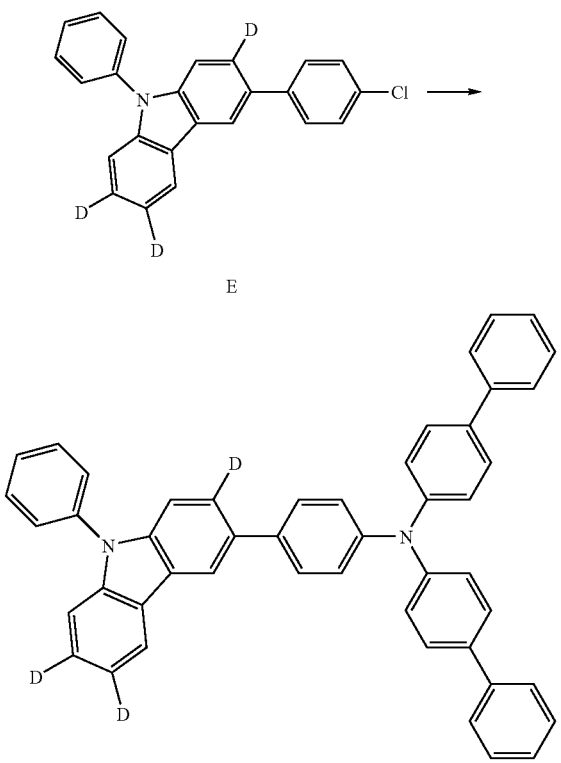

Formula 22

EXAMPLE 7-1

Manufacturing of the Compound A

The compound B (10 g, 30.7 mmol) that was manufactured in Example 5-2, iodo benzene (8.2 g, 40 mmol), and potassium carbonate (8.3 g, 60 mmol) were suspended in dimethylacetamide (100 ml), copper (2 g, 31.5 mmol) was put thereinto, and they were refluxed for 12 hours under a nitrogen atmosphere. After the reaction was finished, it was cooled to normal temperature, and was filtered. The filtration solution was poured into water, extracted by using chloroform, and dried by using anhydrous magnesium sulfate. After it was distilled under the reduced pressure, it was subjected to the column purification by using a hexane/tetrahydrofuran=12/1 solvent to obtain a compound A (6.8 g, yield 55%). MS: $[M+H]^+$=402

EXAMPLE 7-2

Manufacturing of the Compound B

The compound A (6 g, 15 mmol) that was manufactured in Example 7-1 was dissolved in anhydrous tetrahydrofuran (100 ml), n-butyl lithium (2.5M hexane solution, 13.2 ml, 33 mmol) was added dropwise at −78° C., and after 1 hour, heavy water (1.2 g, 60 mmol) was put thereinto. After it was heated to normal temperature, water (30 ml) was put thereinto, it was agitated, and the organic layer was separated. The organic layer was dried by using anhydrous magnesium sulfate, filtered, and distilled under the reduced pressure. It was recrystallized by using ethanol to obtain a compound E (2.6 g, yield 71%). MS: $[M+H]^+$=246

EXAMPLE 7-3

Manufacturing of the Compound C

The compound B (2.5 g, 10.2 mmol) that was manufactured in Example 7-2 was dissolved in chloroform (60 mL), N-bromosuccinimide (3.9 g, 22 mmol) was added thereto, and they were agitated for 5 hours at normal temperature. Distilled water was put into the reaction solution and the organic layer was extracted. It was distilled under the reduced pressure, and recrystallized by using tetrahydrofuran and ethanol to obtain a compound C (3.7 g, yield 90%). MS: $[M+H]^+$=404

EXAMPLE 7-4

Manufacturing of the Compound D

The compound C (3.5 g, 8.7 mmol) that was manufactured in Example 7-3 was dissolved in anhydrous tetrahydrofuran (80 ml), n-butyl lithium (2.5M hexane solution, 3.5 ml, 8.7 mmol) was added dropwise at −78° C., and after 1 hour, heavy water (0.4 g, 20 mmol) was put thereinto. After it was heated to normal temperature, water (20 ml) was put thereinto, it was agitated, and the organic layer was separated. The organic layer was dried by using anhydrous magnesium sulfate, filtered, and distilled under the reduced pressure. It was recrystallized by using hexane to obtain a compound D (1.3 g, yield 46%). MS: $[M+H]^+$=326

EXAMPLE 7-5

Manufacturing of the Compound E

After the compound D (1.2 g, 3.7 mmol) that was manufactured in Example 7-4 and 4-chlorophenyl boronic acid (0.69 g, 4.4 mmol) were dissolved in tetrahydrofuran (70 ml), tetrakis(triphenylphosphine)palladium (0.09 g, 0.07 mmol) and 2N potassium carbonate aqueous solution were put thereinto and refluxed for 12 hours. After the reaction was finished, it was cooled to normal temperature, and the organic layer was separated and dried by using anhydrous magnesium sulfate. After it was distilled under the reduced pressure, it was recrystallized by using tetrahydrofuran and ethanol to obtain a compound F (0.95 g, yield 72%). MS: [M+H]$^+$=357

EXAMPLE 7-6

Manufacturing of the Formula 22

The compound E (0.9 g, 2.5 mmol) that was manufactured in Example 7-5 and bis(4-biphenylyl)amine (0.87 g, 2.7 mmol) were dissolved in xylene (50 ml), sodium-tertiary-butoxide (0.32 g, 3.3 mmol) and bis(tri tertiary-butyl phosphine)palladium (0.02 g, 0.04 mmol) were added thereto, and they were refluxed for 5 hours under a nitrogen atmosphere. After the reaction was finished, it was cooled to normal temperature, an acidic white clay was put, and then agitated. After it was filtered, it was distilled under the reduced pressure and recrystallized by using tetrahydrofuran and ethanol to obtain Formula 22 (1.2 g, yield 75%). MS: [M+H]$^+$=642

EXAMPLE 8

Manufacturing of the Compound Represented by Formula 27

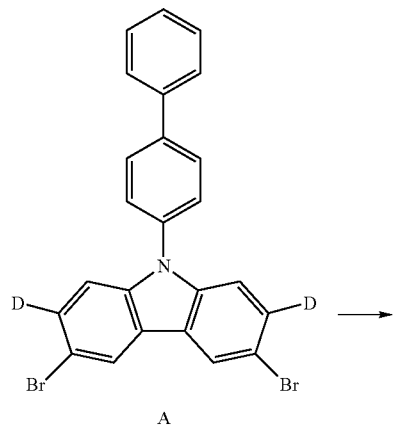

A

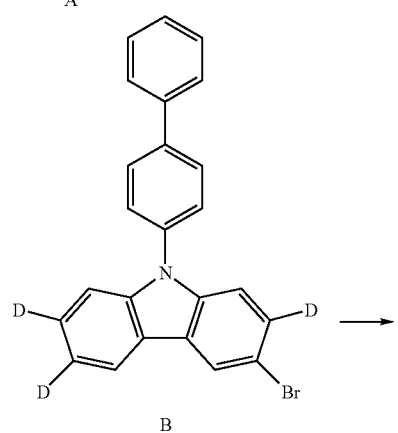

B

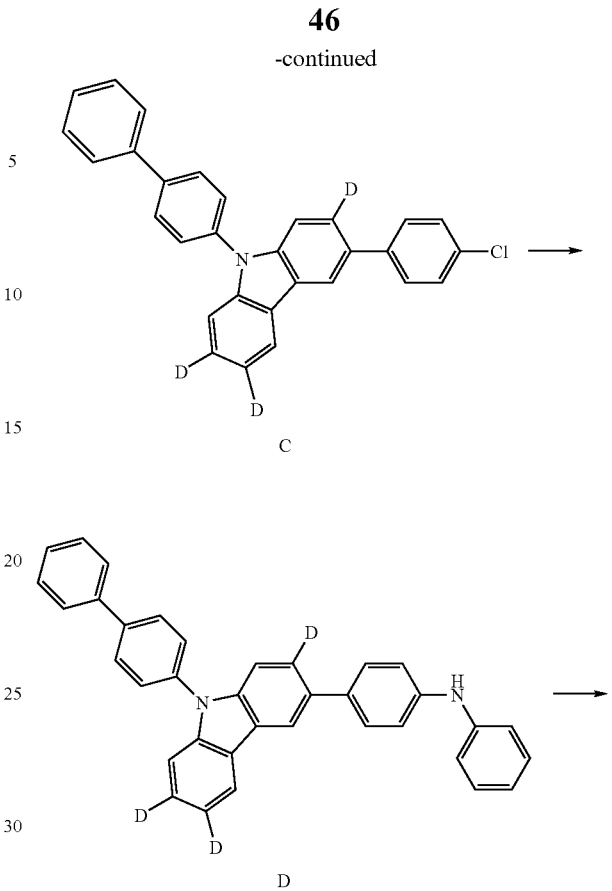

Formula 27

EXAMPLE 8-1

Manufacturing of the Compound A

The compound D (5 g, 15.6 mmol) that was manufactured in Example 5-4 was dissolved in chloroform (80 mL), N-bromosuccinimide (5.7 g, 32 mmol) was added thereto, and they were agitated for 5 hours at normal temperature After the reaction was finished, the manufactured solid was filtered. It was sequentially washed by using water and ethanol, and dried to obtain a compound A (6.8 g, yield 91%). MS: [M+H]$^+$=480

EXAMPLE 8-2

Manufacturing of the Compound B

The compound A (6.5 g, 13.6 mmol) that was manufactured in Example 8-1 was dissolved in anhydrous tetrahydrofuran (100 ml), n-butyl lithium (2.5M hexane solution, 5.4 ml, 13.6 mmol) was added dropwise at −78° C., and after 1 hour, heavy water (0.5 g, 25 mmol) was put thereinto. After it was heated to normal temperature, water (20 ml) was put thereinto, it was agitated, and the organic layer was separated. The organic layer was dried by using anhydrous magnesium sulfate, filtered, and distilled under the reduced pressure. It was recrystallized by using tetrahydrofuran and ethanol to obtain a compound B (2.9 g, yield 53%). MS: $[M+H]^+=402$

EXAMPLE 8-3

Manufacturing of the Compound C

After the compound B (2.5 g, 6.2 mmol) that was manufactured in Example 8-2 and 4-chlorophenyl boronic acid (1.1 g, 7 mmol) were dissolved in tetrahydrofuran (70 ml), tetrakis(triphenylphosphine)palladium (0.09 g, 0.07 mmol) and 2N potassium carbonate aqueous solution were put thereinto and refluxed for 12 hours. After the reaction was finished, it was cooled to normal temperature, and the organic layer was separated and dried by using anhydrous magnesium sulfate. After it was distilled under the reduced pressure, it was recrystallized by using tetrahydrofuran and ethanol to obtain a compound C (2.1 g, yield 78%). MS: $[M+H]^+=433$

EXAMPLE 8-4

Manufacturing of the Compound D

The compound C (2 g, 4.6 mmol) that was manufactured in Example 8-3 and aniline (0.51 g, 5.5 mmol) were dissolved in xylene (60 ml), sodium-tertiary-butoxide (0.58 g, 6 mmol) and bis(tri tertiary-butyl phosphine)palladium (0.03 g, 0.06 mmol) were added thereto, and they were refluxed for 5 hours under a nitrogen atmosphere. After the reaction was finished, it was cooled to normal temperature, an acidic white clay was put, and then agitated. After it was filtered, it was distilled under the reduced pressure and subjected to column purification by using a hexane/tetrahydrofuran=7/1 solvent to obtain the compound D (1.6 g, yield 71%). MS: $[M+H]^+=490$

EXAMPLE 8-5

Manufacturing of Formula 27

The compound D (1.5 g, 3.1 mmol) that was manufactured in Example 8-4 and 3-bromo-N-phenylcarbazole (1 g, 3.1 mmol) were dissolved in xylene (60 ml), sodium-tertiary-butoxide (0.38 g, 4 mmol) and bis(tri tertiary-butyl phosphine)palladium (0.02 g, 0.04 mmol) were added thereto, and they were refluxed for 5 hours under a nitrogen atmosphere. After the reaction was finished, it was cooled to normal temperature, an acidic white clay was put, and then agitated. After it was filtered, it was distilled under the reduced pressure and subjected to column purification by using a hexane/tetrahydrofuran=6/1 solvent to obtain Formula 27 (1.5 g, yield 66%). MS: $[M+H]^+=731$

EXAMPLE 9

Manufacturing of the Compound represented by Formula 32

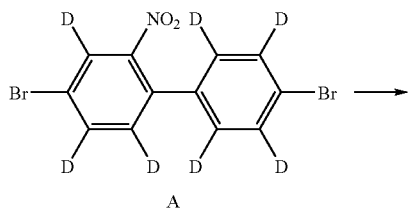

A

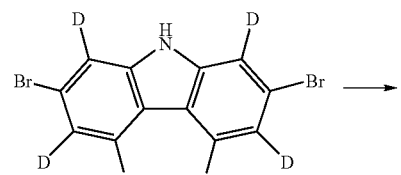

B

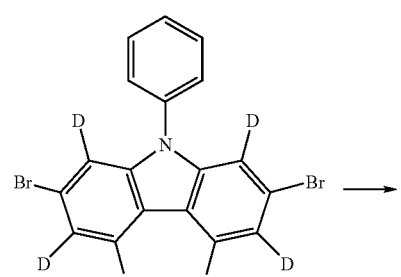

C

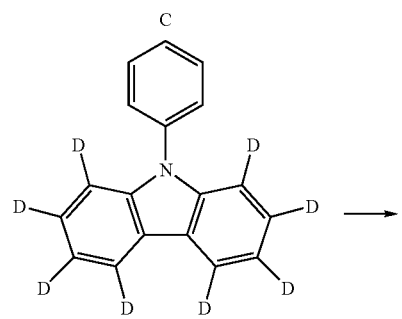

D

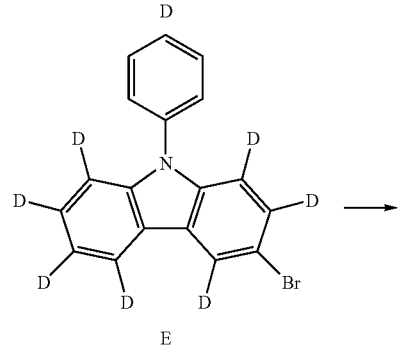

E

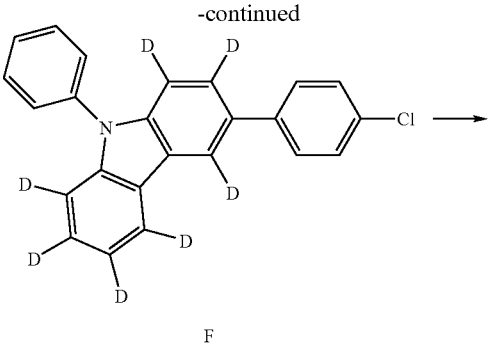

F

Formula 32

EXAMPLE 9-1

Manufacturing of the Compound A

Into the solution in which a nitric acid (50 ml) and an acetic acid (50 ml) were mixed with each other, 4,4'-dibromobiphenyl-D8 (20 g, 62.4 mmol) was slowly put while it was suspended in dichloromethane (60 ml) and an acetic acid (400 ml). After 18 hours, the reaction solution was poured into the sodium hydroxide aqueous solution to neutralize it, and it was extracted by using dichloromethane. The organic layer was dried by using anhydrous magnesium sulfate and distilled under the reduced pressure, recrystallized by using methanol to obtain a compound A (17.5 g, yield 77%). MS: $[M+H]^+=365$

EXAMPLE 9-2

Manufacturing of the Compound B

The compound A (17 g, 46.7 mmol) that was manufactured in Example 9-1 and triphenyl phosphine (30.6 g, 116.8 mmol) were mixed with each other, and it was refluxed while o-dichlorobenzene (130 ml) was put thereinto and agitated. After the reaction was finished, it was cooled to normal temperature and distilled under the reduced pressure. It was subjected to the column purification by using a ligroin/dichloromethane=3/1 solvent to obtain a compound B (10.9 g, yield 71%). MS: $[M+H]^+=332$

EXAMPLE 9-3

Manufacturing of the Compound C

The compound B(10 g, 30.7 mmol) that was manufactured in Example 9-2, iodo benzene(7.3 g, 36 mmol), potassium carbonate(8.3 g, 60 mmol) were suspended in dimethyl acetamide (100 ml), copper (2 g, 31.5 mmol) was put thereinto, and they were refluxed for 12 hours under a nitrogen atmosphere. After the reaction was finished, it was cooled to normal temperature, and was filtered. The filtration solution was poured into water, extracted by using chloroform, and dried by using anhydrous magnesium sulfate. After it was distilled under the reduced pressure, it was subjected to the column purification by using a hexane/tetrahydrofuran=10/1 solvent to obtain a compound C (6.1 g, yield 50%). MS: $[M+H]^+=408$

EXAMPLE 9-4

Manufacturing of the Compound D

The compound C (6 g, 14.7 mmol) that was manufactured in Example 9-3 was dissolved in anhydrous tetrahydrofuran (120 ml), n-butyl lithium (2.5M hexane solution, 12.9 ml, 32.3 mmol) was added dropwise at −78° C., and after 1 hour, heavy water (1.2 g, 60 mmol) was put thereinto. After it was heated to normal temperature, water (30 ml) was put thereinto, it was agitated, and the organic layer was separated. The organic layer was dried by using anhydrous magnesium sulfate, filtered, and distilled under the reduced pressure. It was recrystallized by using and ethanol to obtain a compound D (2.3 g, yield 62%). MS: $[M+H]^+=252$

EXAMPLE 9-5

Manufacturing of the Compound E

The compound D (2 g, 8 mmol) that was manufactured in Example 9-4 was dissolved in chloroform (60 mL), N-bromosuccinimide (1.4 g, 8 mmol) was added thereto, and they were agitated for 5 hours at normal temperature. Distilled water was put into the reaction solution and the organic layer was extracted. It was distilled under the reduced pressure, and the next reaction was performed without the purification process.

EXAMPLE 9-6

Manufacturing of the Compound F

After the compound E that was manufactured in Example 9-5 and 4-chlorophenyl boronic acid (1.5 g, 9.6 mmol) were dissolved in tetrahydrofuran (80 ml), tetrakis(triphenylphosphine)palladium (0.18 g, 0.16 mmol) and 2N potassium carbonate aqueous solution were put thereinto and refluxed for 12 hours. After the reaction was finished, it was cooled to normal temperature, and the organic layer was separated and dried by using anhydrous magnesium sulfate. After it was distilled under the reduced pressure, it was subjected to the column purification by using a hexane/tetrahydrofuran=12/1 solvent to obtain a compound F (1.1 g, yield 39%). MS: $[M+H]^+=361$

EXAMPLE 9-7

Manufacturing of Formula 32

The compound F (1 g, 2.8 mmol) that was manufactured in Example 9-6 and bis(4-biphenylyl)amine (0.9 g, 2.8 mmol) were dissolved in xylene (50 ml), sodium-tertiary-butoxide (0.35 g, 3.6 mmol) and bis(tri tertiary-butyl phosphine)palladium (0.02 g, 0.04 mmol) were added thereto, and they were refluxed for 5 hours under a nitrogen atmosphere. After the reaction was finished, it was cooled to normal temperature, an acidic white clay was put, and then agitated. After it was filtered, it was distilled under the reduced pressure and recrystallized by using tetrahydrofuran and ethanol to obtain Formula 32 (1.2 g, yield 66%). MS: $[M+H]^+=646$

EXPERIMENTAL EXAMPLE 1

A glass substrate, on which ITO (indium tin oxide) was applied to a thickness of 1500 Å to form a thin film, was put in distilled water, in which a detergent was dissolved, and washed using ultrasonic waves. In connection with this, a product manufactured by Fischer Inc. was used as the detergent, and distilled water was produced by filtering twice using a filter manufactured by Millipore Inc. After ITO was washed for 30 min, ultrasonic washing was conducted twice using distilled water for 10 min. After the washing using distilled water was completed, ultrasonic washing was conducted using isopropyl alcohol, acetone, and methanol solvents, and drying was then conducted. Next, it was transported to a plasma washing machine. In addition, the substrate was washed using oxygen plasma for 5 min, and then transported to a vacuum evaporator.

Hexanitrile hexaazatriphenylene (hereinafter, referred to as "HAT") of the following Formula was vacuum deposited to a thickness of 500 Å by heating on a transparent ITO electrode, which was prepared through the above procedure, so as to form a hole injection layer.

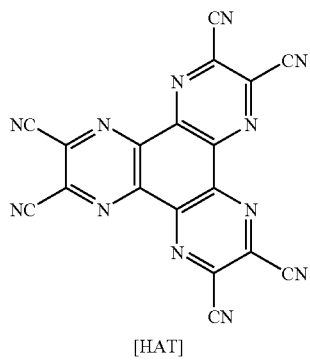

[HAT]

The compound of Formula 2, which was prepared in Example 1, was vacuum deposited to a thickness of 400 Å by heating on the hole injection layer so as to form a hole transport layer.

Subsequently, on the hole transport layer, GH and GD as described below were vacuum deposited to a film thickness of 300 Å at a film thickness ratio of 20:1 so as to form a light emitting layer.

[GH]

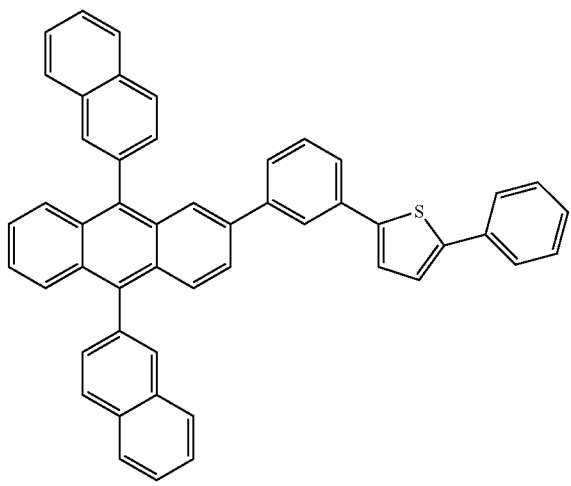

[GD]

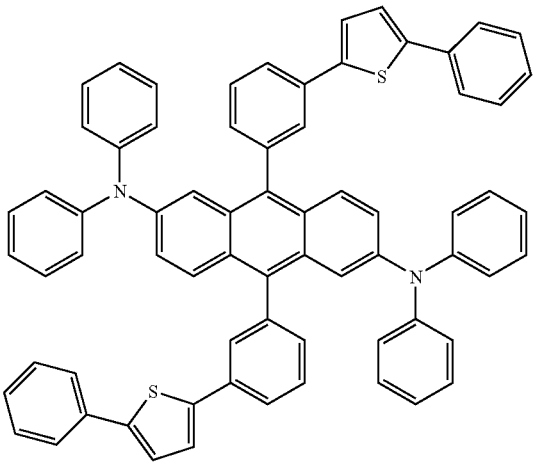

On the light emitting layer, the electron transport material as described below was vacuum deposited to a thickness of 200 Å so as to form an electron injection layer and a electron transport layer.

[Electron Transport Material]

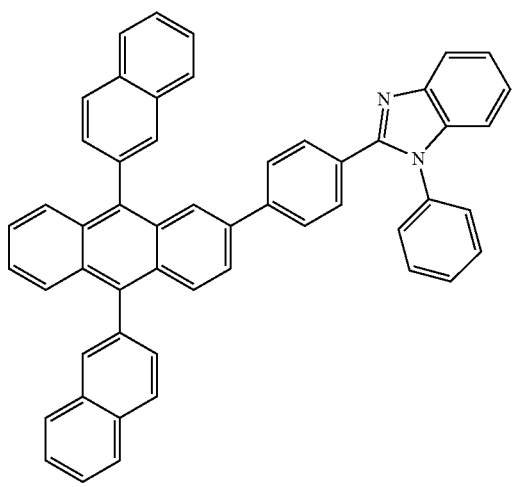 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]

Lithium fluoride (LiF) having a thickness of 12 Å and aluminum having a thickness of 2000 Å were sequentially deposited on the electron injection layer and the electron transport layer to form a cathode.

In the above procedure, the deposition speed of an organic material was maintained at 0.4 to 0.7 Å/sec, lithium fluoride and aluminum were deposited at speeds of 0.3 Å/sec and 2 Å/sec, respectively, on the cathode, and in the deposition, a vacuum was maintained at $2 \times 10^{-7}$ to $5 \times 10^{-8}$ torr.

A forward current density of 4.6 V was applied to the organic light emitting device manufactured in the above, and as a result, the green light in which the color coordinate was (0.32, 0.65) at a current density of 50 mA/cm$^2$ was observed at 28 cd/A, and a life span to the luminance of 90% was 300 hours.

EXPERIMENTAL EXAMPLE 2

The same process was performed to manufacture an organic EL device, except that the compound of Formula 3 was used instead of the compound of Formula 2 in Experimental Example 1.

A forward current density of 4.7 V was applied to the light emitting device manufactured in the above, and as a result, the green light in which the color coordinate was (0.31, 0.64) at a current density of 50 mA/cm$^2$ was observed at 30 cd/A, and a life span to the luminance of 90% was 310 hours.

EXPERIMENTAL EXAMPLE 3

The same process was performed to manufacture an organic EL device, except that the compound of Formula 4 was used instead of the compound of Formula 2 in Experimental Example 1.

A forward current density of 4.5 V was applied to the light emitting device manufactured in the above, and as a result, the green light in which the color coordinate was (0.32, 0.65) at a current density of 50 mA/cm$^2$ was observed at 29 cd/A, and a life span to the luminance of 90% was 340 hours.

EXPERIMENTAL EXAMPLE 4

The same process was performed to manufacture an organic EL device, except that the compound of Formula 7 was used instead of the compound of Formula 2 in Experimental Example 1.

A forward current density of 4.6 V was applied to the light emitting device manufactured in the above, and as a result, the green light in which the color coordinate was (0.31, 0.65) at a current density of 50 mA/cm$^2$ was observed at 29 cd/A, and a life span to the luminance of 90% was 320 hours.

EXPERIMENTAL EXAMPLE 5

The same process was performed to manufacture an organic EL device, except that the compound of Formula 13 was used instead of the compound of Formula 2 in Experimental Example 1.

A forward current density of 4.7 V was applied to the light emitting device manufactured in the above, and as a result, the green light in which the color coordinate was (0.32, 0.64) at a current density of 50 mA/cm$^2$ was observed at 30 cd/A, and a life span to the luminance of 90% was 350 hours.

EXPERIMENTAL EXAMPLE 6

The same process was performed to manufacture an organic EL device, except that the compound of Formula 17 was used instead of the compound of Formula 2 in Experimental Example 1.

A forward current density of 4.6 V was applied to the light emitting device manufactured in the above, and as a result, the green light in which the color coordinate was (0.31, 0.65) at a current density of 50 mA/cm$^2$ was observed at 29 cd/A, and a life span to the luminance of 90% was 330 hours.

EXPERIMENTAL EXAMPLE 7

The same process was performed to manufacture an organic EL device, except that the compound of Formula 22 was used instead of the compound of Formula 2 in Experimental Example 1.

A forward current density of 4.5 V was applied to the light emitting device manufactured in the above, and as a result, the green light in which the color coordinate was (0.32, 0.65) at a current density of 50 mA/cm$^2$ was observed at 29 cd/A, and a life span to the luminance of 90% was 370 hours.

EXPERIMENTAL EXAMPLE 8

The same process was performed to manufacture an organic EL device, except that the compound of Formula 27 was used instead of the compound of Formula 2 in Experimental Example 1.

A forward current density of 4.6 V was applied to the light emitting device manufactured in the above, and as a result, the green light in which the color coordinate was (0.32, 0.64) at a current density of 50 mA/cm$^2$ was observed at 29 cd/A, and a life span to the luminance of 90% was 360 hours.

EXPERIMENTAL EXAMPLE 9

The same process was performed to manufacture an organic EL device, except that the compound of Formula 32 was used instead of the compound of Formula 2 in Experimental Example 1.

A forward current density of 4.7 V was applied to the light emitting device manufactured in the above, and as a result, the green light in which the color coordinate was (0.32, 0.65) at a current density of 50 mA/cm$^2$ was observed at 30 cd/A, and a life span to the luminance of 90% was 390 hours.

COMPARATIVE EXAMPLE 1

The same process was performed to manufacture an organic EL device, except that 4,4'-bis[N-(1-naphthyl)-N-phenylamino]biphenyl (NPB) of the following Formula was used instead of the compound of Formula 2 in Experimental Example 1.

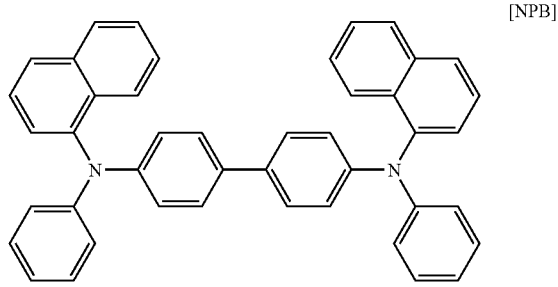 [SMILES: c1ccc(N(c2ccc(-c3ccc(N(c4ccccc4)c4cccc5ccccc45)cc3)cc2)c2cccc3ccccc23)cc1]

[NPB]

A forward current density of 4.5 V was applied to the light emitting device manufactured in the above, and as a result, the green light in which the color coordinate was (0.32, 0.64) at a current density of 50 mA/cm$^2$ was observed at 27 cd/A, and a life span to the luminance of 90% was 140 hours.

COMPARATIVE EXAMPLE 2

The same process was performed to manufacture an organic EL device, except that the compound of the following Formula HT1 was used instead of the compound of Formula 2 in Experimental Example 1.

[HT1]

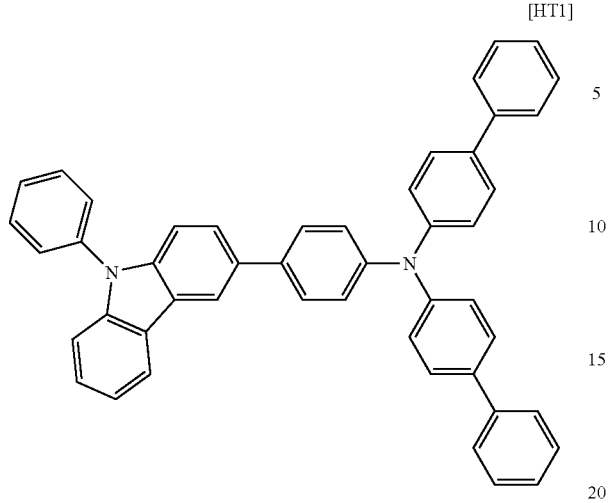

A forward current density of 4.6 V was applied to the light emitting device manufactured in the above, and as a result, the green light in which the color coordinate was (0.31, 0.64) at a current density of 50 mA/cm² was observed at 28 cd/A, and a life span to the luminance of 90% was 250 hours.

COMPARATIVE EXAMPLE 3

The same process was performed to manufacture an organic EL device, except that the compound of the following Formula HT2 was used instead of the compound of Formula 2 in Experimental Example 1.

[HT2]

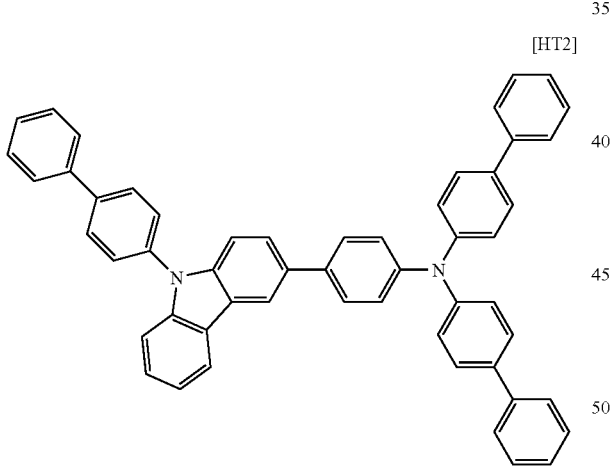

A forward current density of 4.7 V was applied to the light emitting device manufactured in the above, and as a result, the green light in which the color coordinate was (0.32, 0.65) at a current density of 50 mA/cm² was observed at 29 cd/A, and a life span to the luminance of 90% was 270 hours.

INDUSTRIAL APPLICABILITY

The compound of the present invention is used in an organic light emitting device, and the organic light emitting device that includes the compound as an organic material layer largely improves life span, efficiency, electrochemical stability, and thermal stability.

The invention claimed is:
1. A compound of Formula 1:

[Formula 1]

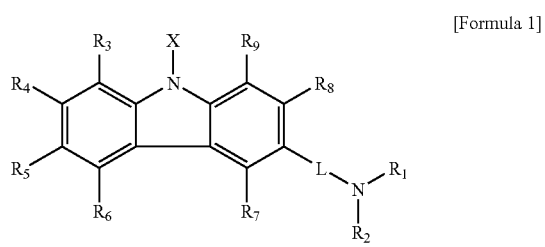

wherein X is selected from the group consisting of hydrogen; an alkyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an alkoxy group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an alkenyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an aryl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an hetero ring group including O, N or S as a heteroatom, which is substituted or unsubstituted with one or more substituent groups selected from the group consisting of a halogen group, an alkyl group, an alkenyl group, an alkoxy group, a substituted or unsubstituted aryl amine group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group! a carbazolyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; a fluorenyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorernyl group, a nitrile group and an acetylene group; —N(R')(R"); a nitrile group; anitro group; a halogen group; —CO—N(R')(R"); and —COO—R', R' and R" are each independently selected from the group consisting of hydrogen, a halogen group, an alkyl group, an alkenyl group, an alkoxy group, a substituted or unsubstituted aryl group, a substituted or unsubstituted arylalkyl group, a substituted or unsubstituted aryl alkenyl group, a substituted or unsubstituted hetero ring group, a substituted or unsubstituted carbazolyl group, a substituted or unsubstituted fluorenyl group, a nitrile group and an acetylene group, L is an arylene group, which is substituted or unsubstituted with one or more substituent groups selected from the group consisting of nitro, nitrile, halogen, an alkyl group, an alkoxy group and an amino group and has 6 to 40 carbon atoms! a divalent hetero ring group, which is substituted or unsubstituted with one or more substituent groups selected from the group consisting of nitro, nitrile, halogen, an alkyl group, an alkoxy group and an amino group; or a fluoarenylene group, which is substituted or unsubstituted with one or more substituent groups selected from the group consisting of nitro, nitrile, halogen, an alkyl group, an alkoxy group and an amino group, $R_1$ and $R_2$ are each independently selected from the group consisting of hydrogen; deuterium; an alkyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group! an alkoxy group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group! an alkenyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an aryl group, which is substituted or unsubstituted with one or more substituent groups selected from the group consisting of a halogen group, an alkyl group, an alkenyl group, an alkoxy group, a substituted or unsubstituted aryl group, a substituted or unsubstituted aryl alkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an hetero ring group including O, N or S as a heteroatom, which is substituted or unsubstituted with one or more substituent groups selected from the group consisting of a halogen group, an alkyl group, an alkenyl group, an aikoxy group, a substituted or unsubstituted arylamine group, a substituted or unsubstituted aryl group, a substituted or unsubstituted arylalkl group, a substituted or unsubstituted arylalkenyl group, a substituted or unsubstituted hetero ring group, a substituted or unsubstituted carbazolvi group, a substituted or unsubstituted fluorenyl group, a nitrile group and an acetylene group; a carbazolyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted unsubstituted fluorenyl group, a nitrile group and an acetylene group; a fluorenyl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an aryloxy group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an arylthio group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group; an alkoxycarbonyl group, which is substituted unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, asubstituted or unsubstituted fluorenyl group, a nitrile group and an acetylene group; a hydroxyl group; a carboxyl group; a nitrile group; a nitro group; a halogen group; —N(R')(R"); a nitrile group; anitro group; a halogen group; —CO—N(R')(R"); and —COO—R', and said $R_1$ and $R_2$ may form an aliphatic or hetero condensation ring in conjunction with adjacent groups, and at least one of $R_3$ to $R_9$ is deuterium, and the remains of $R_3$ to $R_9$ are hydrogen.

2. The compound as set forth in claim 1, wherein X of Formula 1 selected from the group consisting of a phenyl group, a biphenyl group, a terphenyl group, a stilbene group, anaphthyl group, an anthracenyl group, a phenanthrene group, a pyrenyl group, a perylenyl group, a carhazolyl group, a fluorenyl group, a thiophene group, a furan group, a pyrrolyl group, an imidazolyl group, a thiazolyl group, an oxazolyl group, an oxadiazolyl group, atriazolyl group, apyridyl group, a pyradazine group, a quinolinyl group, an isoquinoline group, and an acridyl group.

3. The compound as set forth in claim 1, wherein L is a phenylene group, which is substituted or unsubstituted by one or more substituent groups selected from the group consisting of nitro, nitrile, halogen, an alkyl group, an alkoxy group and an amino group; a divalent hetero ring group including O, N or S and 5 or 6 carbon atoms, which is substituted or unsubstituted by one or more substituent groups selected from the group consisting of nitro, nitrile, halogen, an alkyl group, an alkoxy group and an amino group! or a fluorenylene group, which is substituted or unsubstituted by one or more substituent groups selected from the group consisting of nitro, nitrile, halogen, an alkyl group, an alkoxy group and an amino group.

4. The compound as set forth in claim 1, wherein L is a phenylene group or a fluorenylene group.

5. The compound as set forth in claim 1, wherein $R_1$ and $R_2$ are each independently an aryl group, which is substituted or unsubstituted with one or more substituent groups selected from the group consisting of a halogen group, an alkyl group, an alkenyl group, an alkoxy group, a substituted or unsubstituted aryl group, a substituted or unsubstituted arylalkyl group, a substituted or unsubstituted arylalkenyl group, a substituted or unsubstituted hetero ring group, a substituted or unsubstituted carhazolyl group, a substituted or unsubstituted fluorenyl group, a nitrile group and an acetylene group; or an hetero ring group including O, N or S as aheteroatom, which is substituted or unsubstituted with one or more substituent groups selected from the group consisting of a halogen group, an alkyl group, an alkenyl group, an alkoxy group, a substituted or unsubstituted arylamine group, a substituted or unsubstituted aryl group, a substituted or unsubstituted arylalkyl group, a substituted or unsubstituted arylalkenyl group, a substituted or unsubstituted hetero ring group, a substituted or unsubstituted carbazolyl group, a substituted or unsubstituted fluorenyl group, a nitrile group and an acetylene group.

6. The compound as set forth in claim 1, wherein $R_1$ and $R_2$ are each independently any one of the following groups:

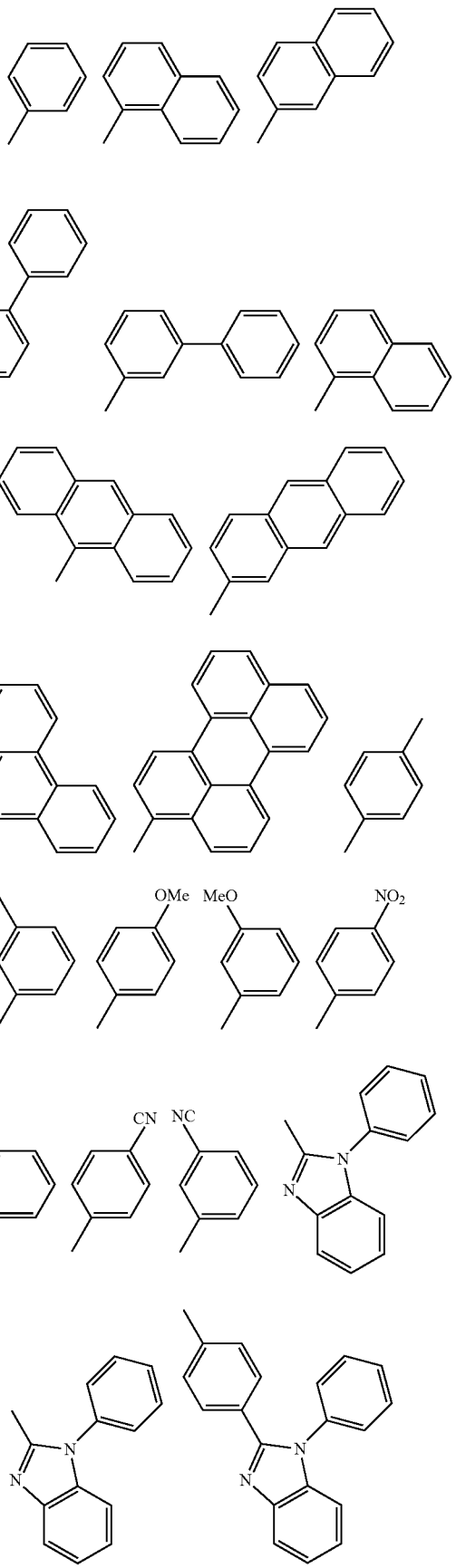

-continued
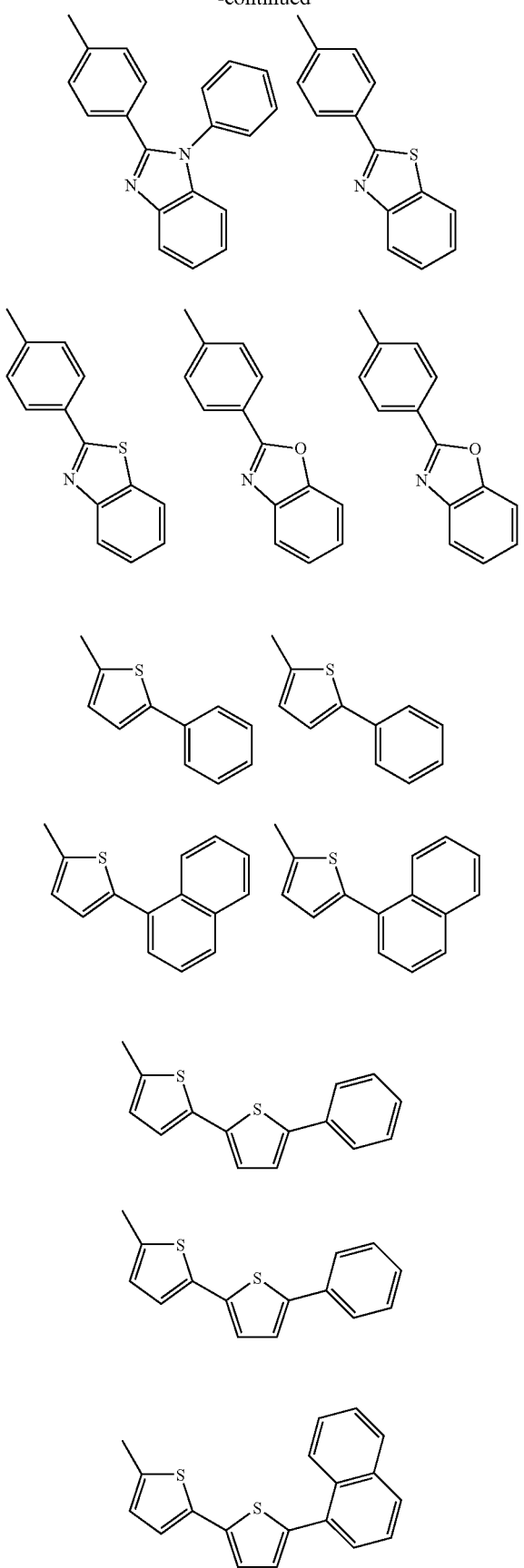
-continued
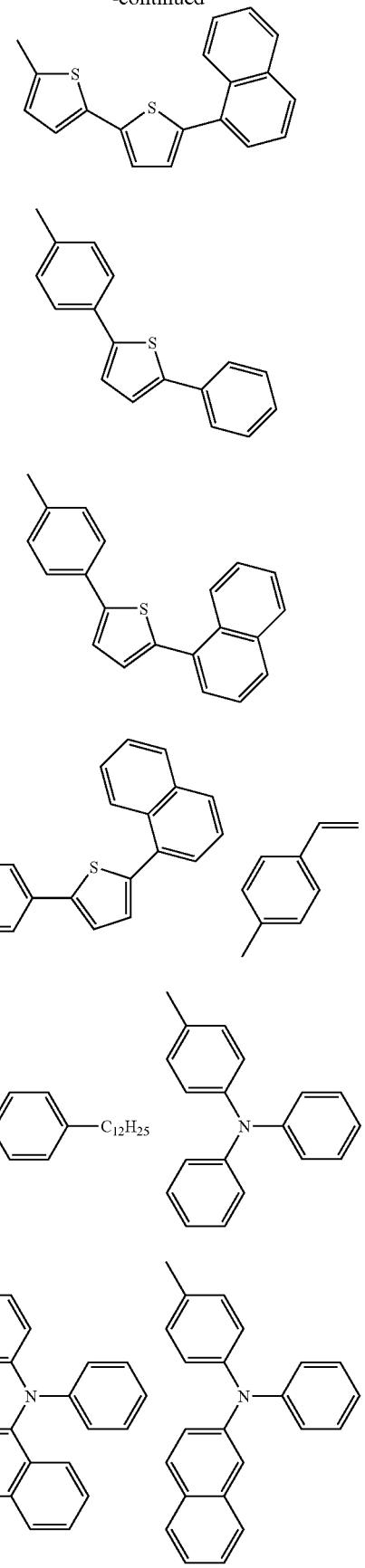

-continued

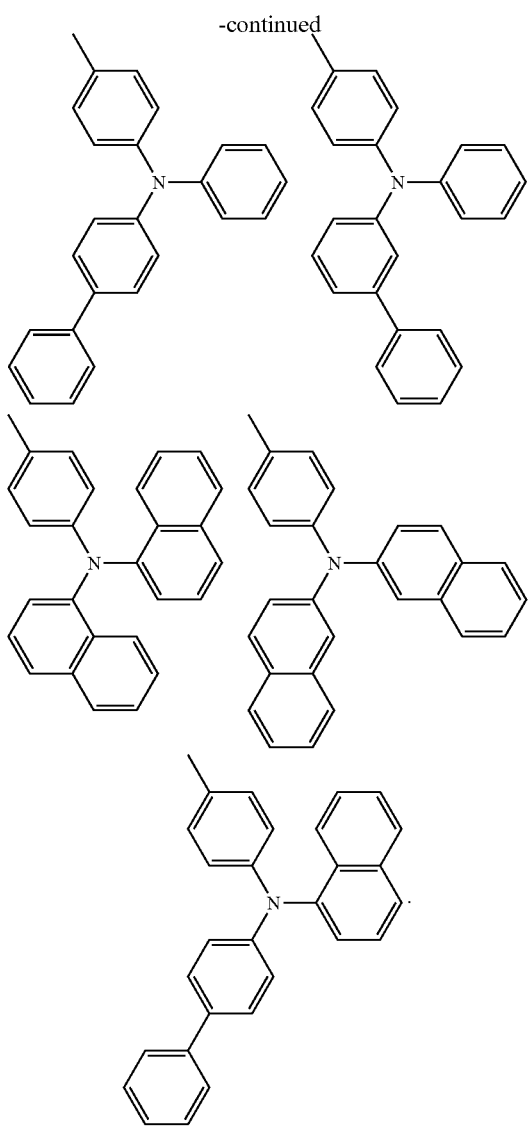

7. An organic light emitting device that includes a first electrode, an organic material layer that includes one or more layers having a light emitting layer, and a second electrode sequentially layered, wherein the organic light emitting device comprises one or more layers of the organic material layer that include the compound of Formula 1 of claim 1, or the compound of Formula 1 into which a thermosetting group or a photocurable functional group is introduced.

8. The organic light emitting device as set forth in claim 7 wherein the organic material layer includes a hole transport layer, and the hole transport layer includes the compound of Formula 1 or the compound of Formula 1 into which a thermosetting group or a photocurable functional group is introduced.

9. The organic light emitting device as set forth in claim 7, wherein the organic material layer includes a hole injection layer, and the hole injection layer includes the compound of Formula 1 or the compound of Formula 1 into which a thermosetting group or a photocurable functional group is introduced.

10. The organic light emitting device as set forth in claim 7, wherein the organic material layer includes a layer that collectively inject and transport a hole, and the layer includes the compound of Formula 1 or the compound of Formula 1 into which a thermosetting group or a photocurable functional group is introduced.

11. The organic light emitting device as set forth in claim 7, wherein the organic material layer includes an electron injection and transport layer, and the electron injection and transport layer includes the compound of Formula 1 or the compound of Formula 1 into which a thermosetting group or a photocurable functional group is introduced.

12. The organic light emitting device as set forth in claim 7, wherein the light emitting layer includes the compound of Formula 1 or the compound of Formula 1 into which a thermosetting group or a photocurable functional group is introduced.

* * * * *